(12) United States Patent
Brookner et al.

(10) Patent No.: US 6,918,880 B2
(45) Date of Patent: Jul. 19, 2005

(54) BIPOLAR RF EXCISION AND ASPIRATION DEVICE AND METHOD FOR ENDOMETRIOSIS REMOVAL

(75) Inventors: Carrie Brookner, Bridgewater, NJ (US); Martin Nohilly, Murray Hill, NJ (US)

(73) Assignee: Ethicon, Inc., Somerville, NJ (US)

( * ) Notice: Subject to any disclaimer, the term of this patent is extended or adjusted under 35 U.S.C. 154(b) by 352 days.

(21) Appl. No.: 10/186,329

(22) Filed: Jun. 28, 2002

(65) Prior Publication Data

US 2004/0002664 A1 Jan. 1, 2004

(51) Int. Cl.[7] .............................................. A61B 10/00
(52) U.S. Cl. .................................................... 600/565
(58) Field of Search .............................. 600/562–567; 128/898; 606/13, 15, 16, 41, 46, 115, 110, 167, 170

(56) References Cited

U.S. PATENT DOCUMENTS

| | | | |
|---|---|---|---|
| 5,437,665 A | | 8/1995 | Munro |
| 5,526,822 A | | 6/1996 | Burbank et al. |
| 5,810,806 A | | 9/1998 | Ritchart et al. |
| 5,997,534 A | | 12/1999 | Tu et al. |
| 6,032,673 A | * | 3/2000 | Savage et al. ............... 128/898 |
| 6,142,957 A | * | 11/2000 | Diamond et al. ............ 600/567 |
| 6,162,214 A | * | 12/2000 | Mueller et al. ................ 606/15 |
| 6,383,198 B1 | * | 5/2002 | Hamilton ..................... 606/115 |

* cited by examiner

Primary Examiner—Max Hindenburg
Assistant Examiner—Brian Szmal

(57) ABSTRACT

An excision and aspiration apparatus adapted to sample a tissue mass includes a receptacle, such as a suction cup, which is adapted to receive a superficial portion only of the total tissue mass. An excision mechanism, such as a cutting wire, excises the superficial portion from the rest of the tissue mass. The excision and aspiration apparatus further includes a suction tube having a receiving channel for collecting the excised superficial portion of the tissue mass, as well as a vacuum source for creating suction within the suction tube that is sufficient to draw the excised superficial portion of the tissue mass into the receiving channel of the suction tube.

15 Claims, 14 Drawing Sheets

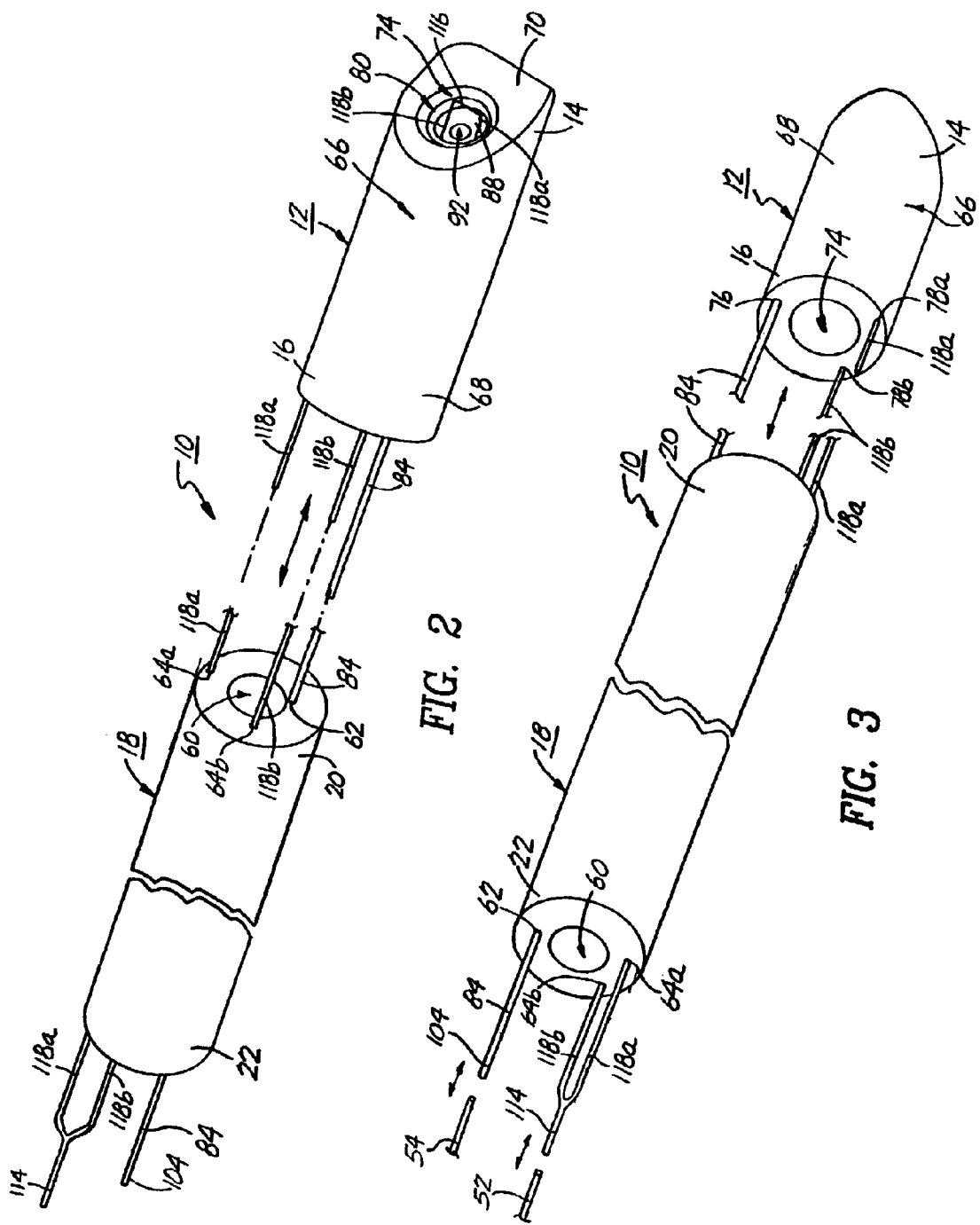

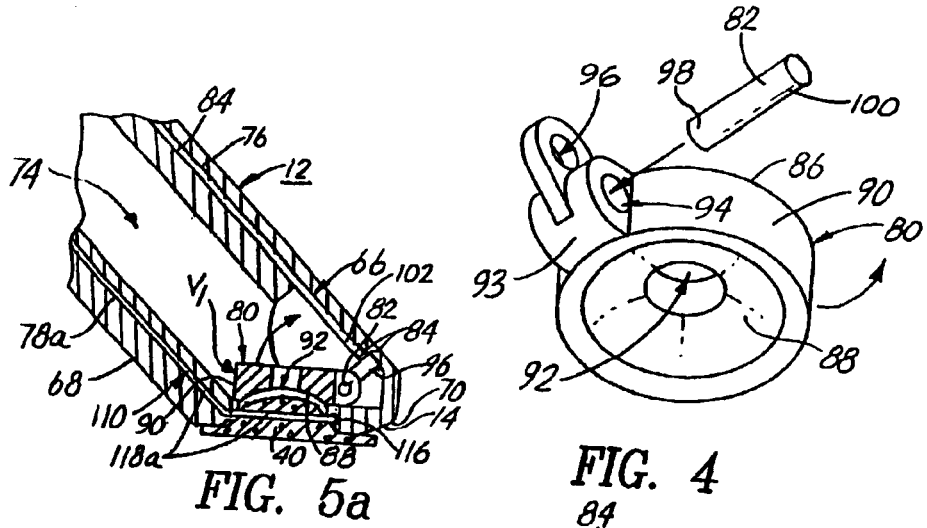
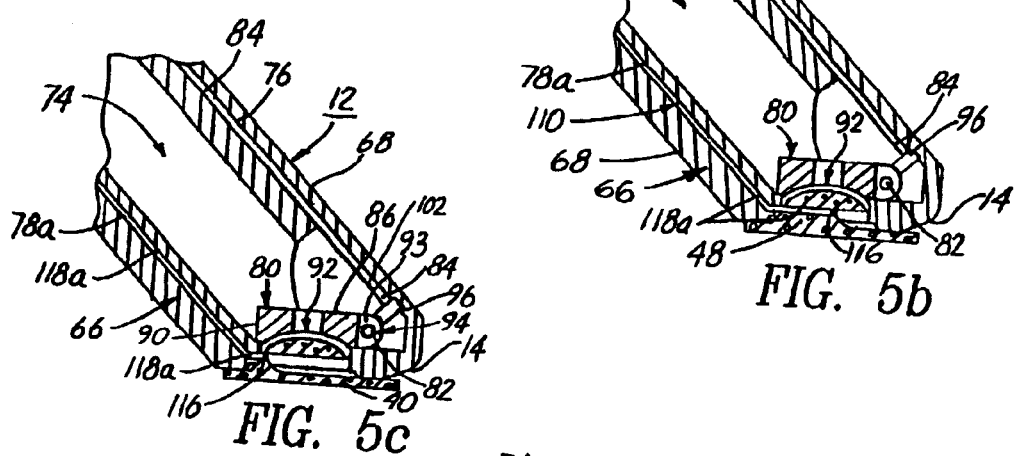
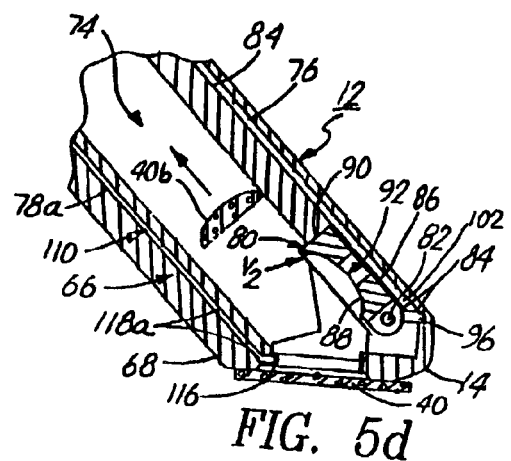

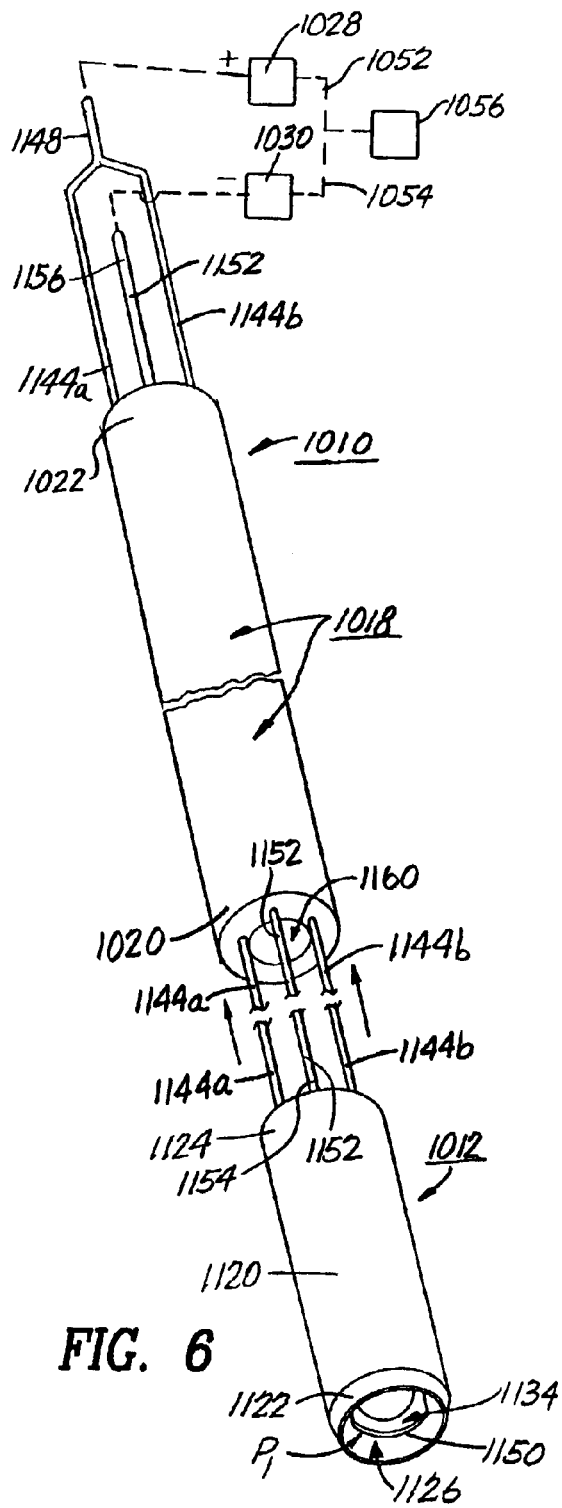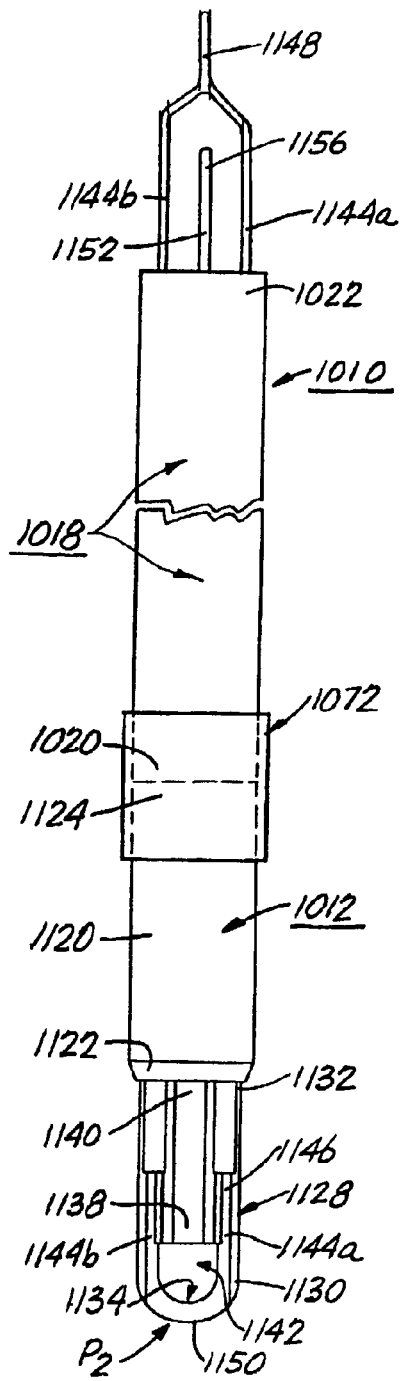
FIG. 6
FIG. 7

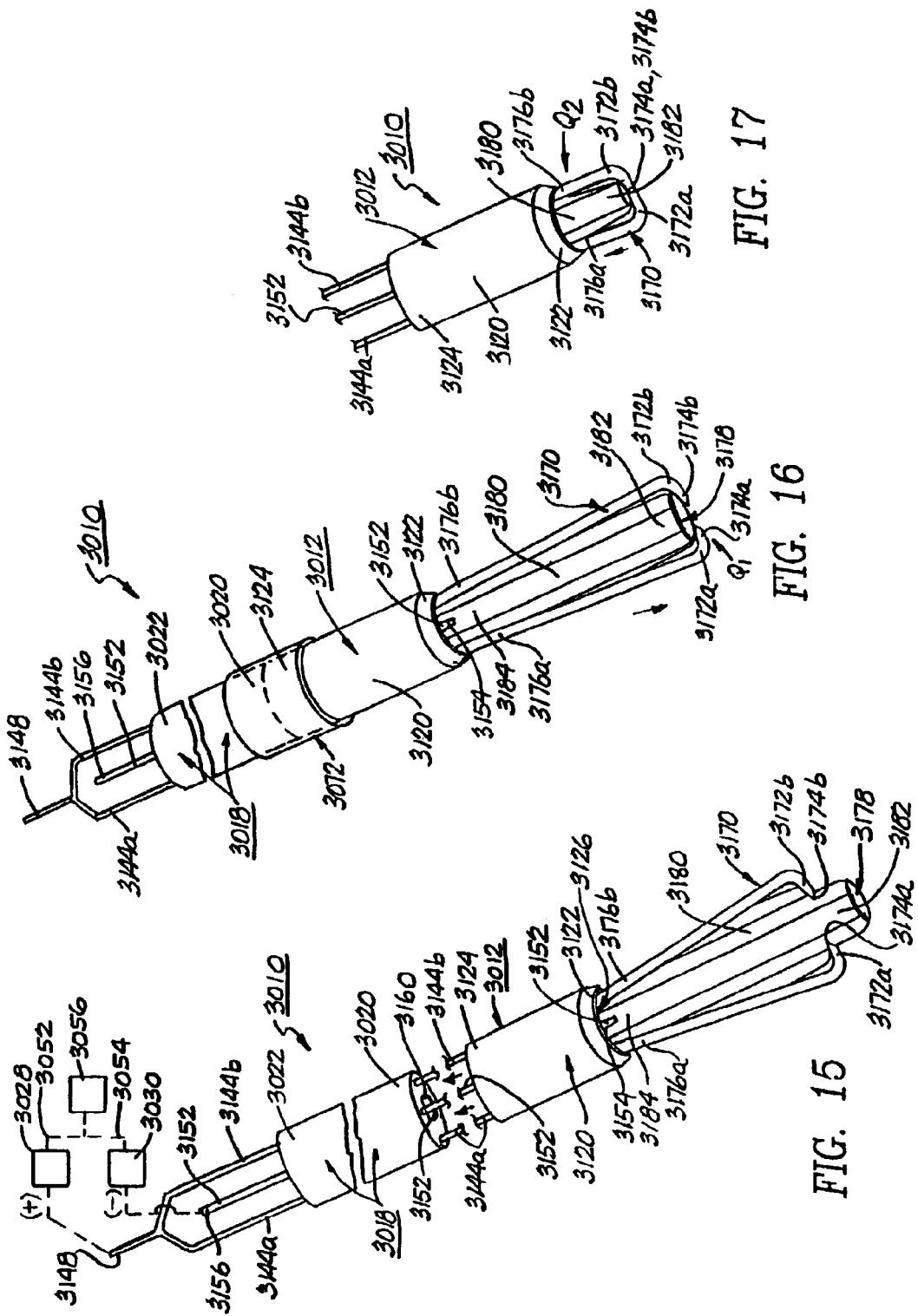

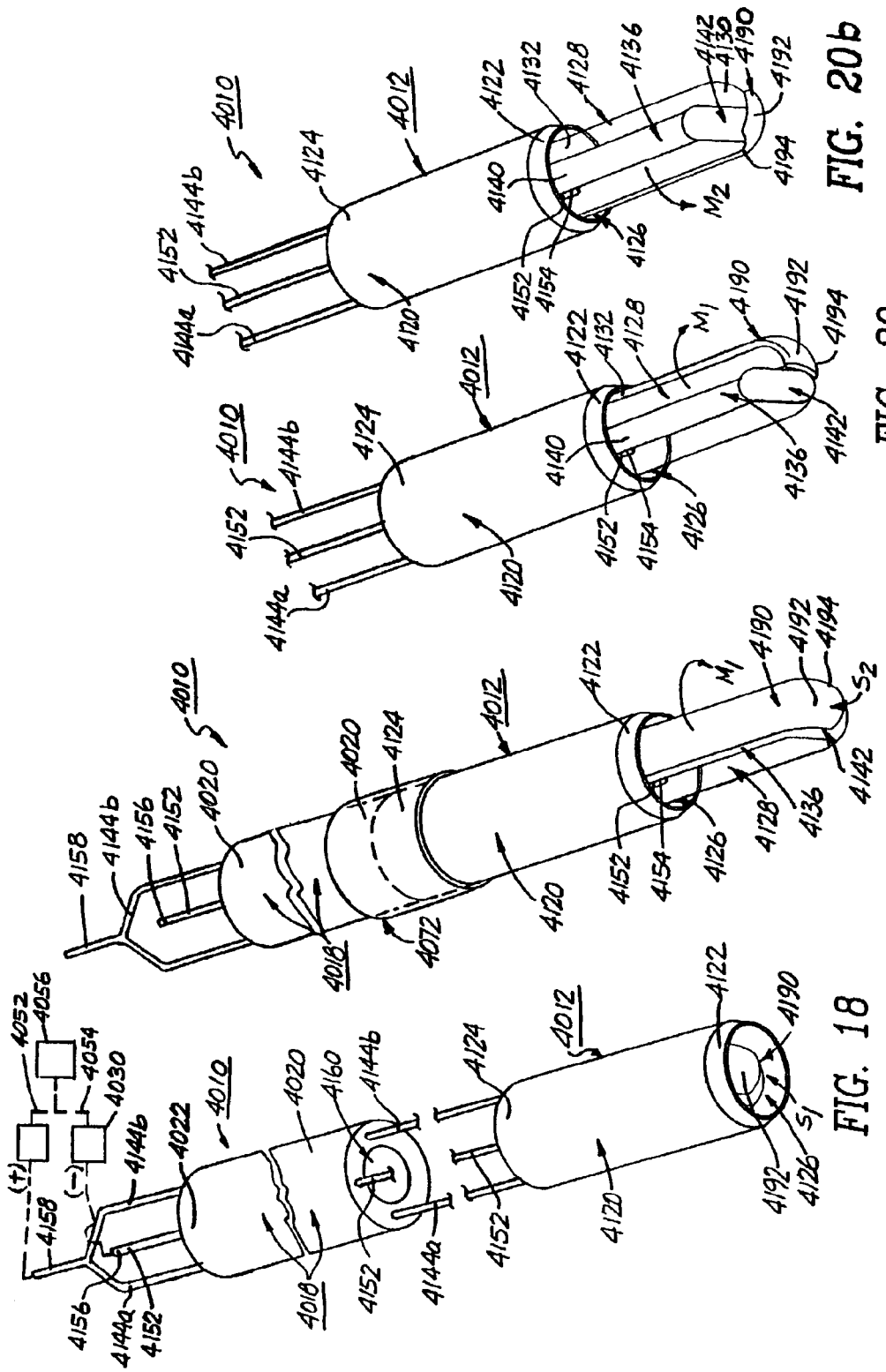

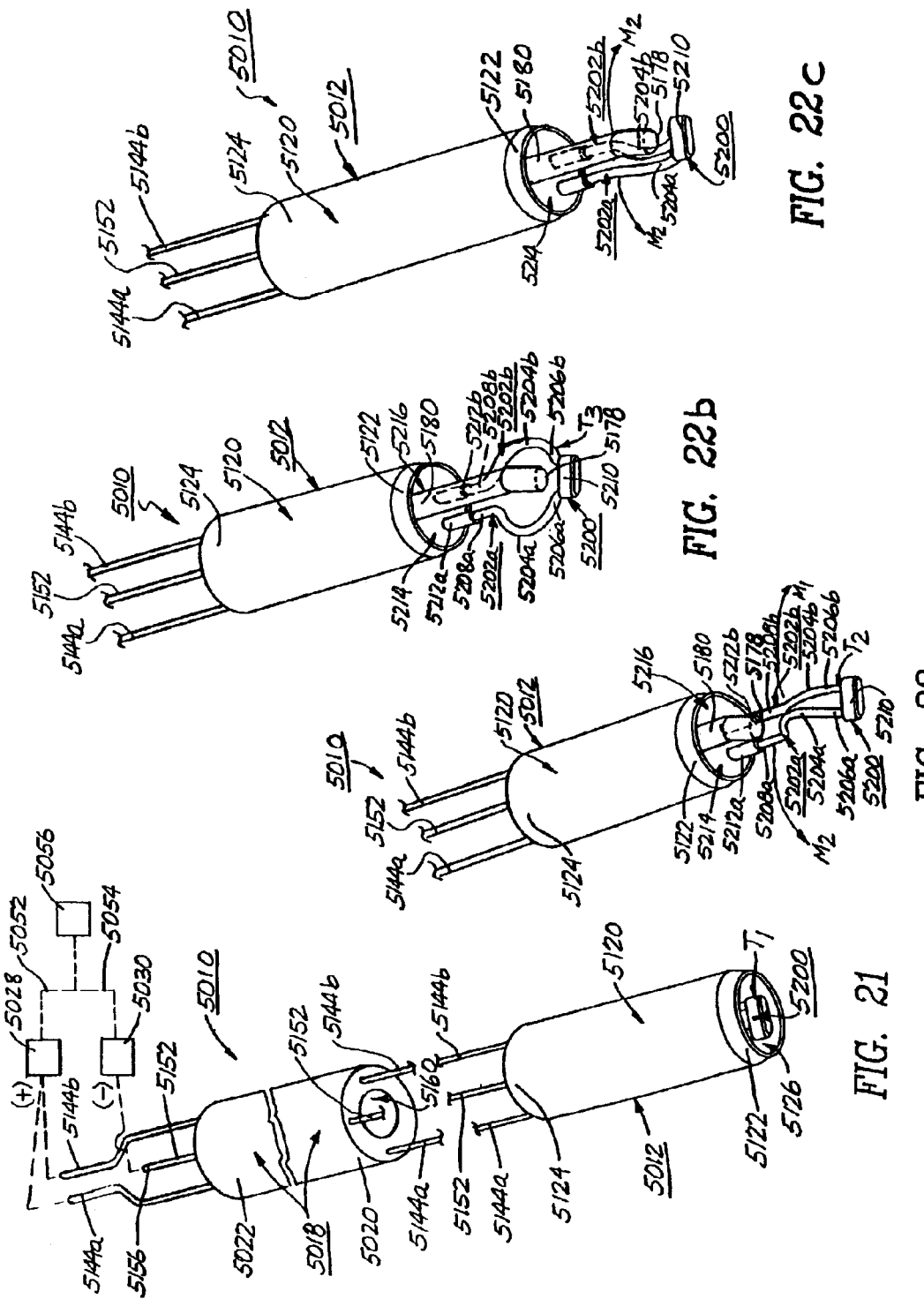

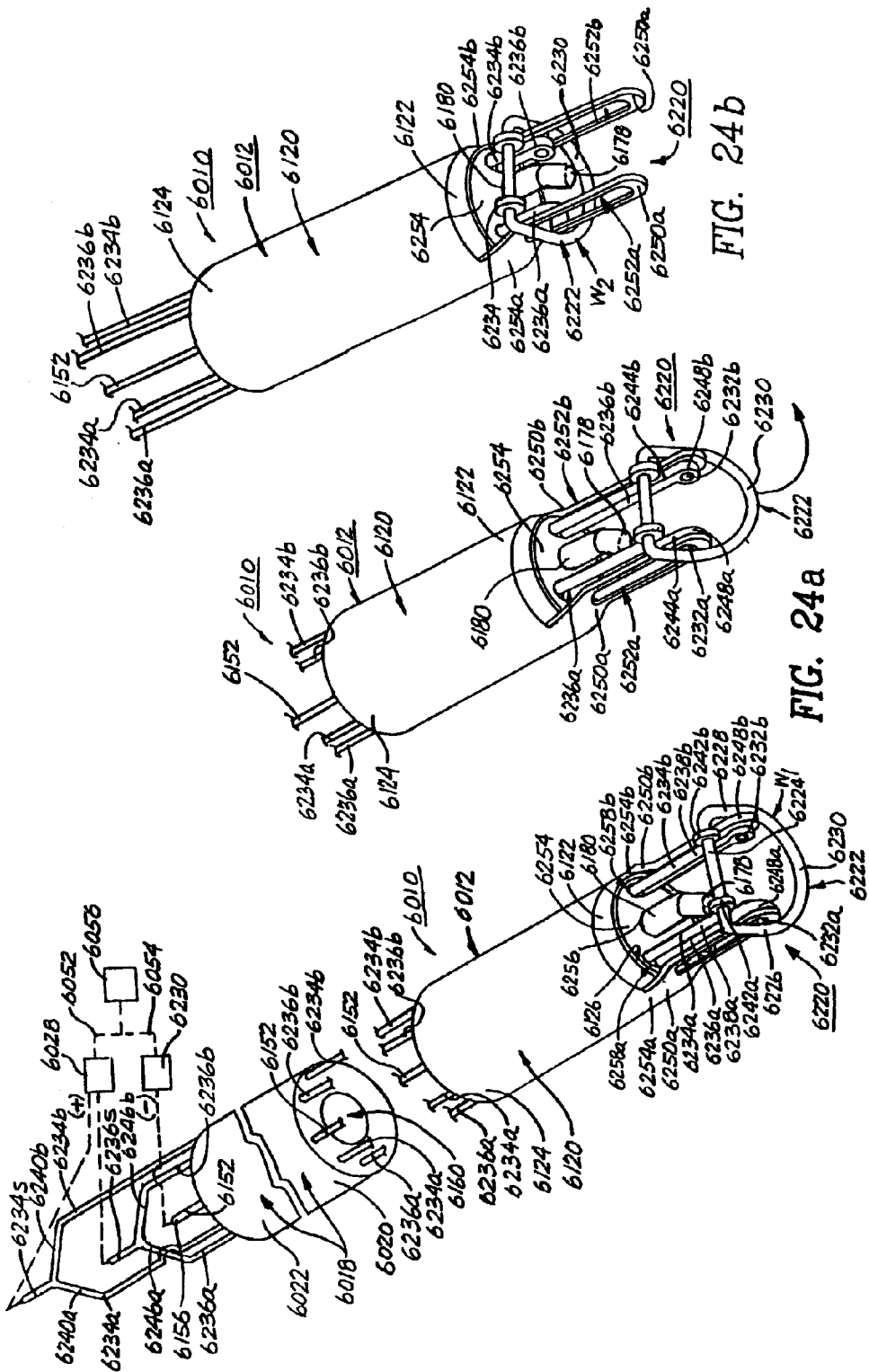

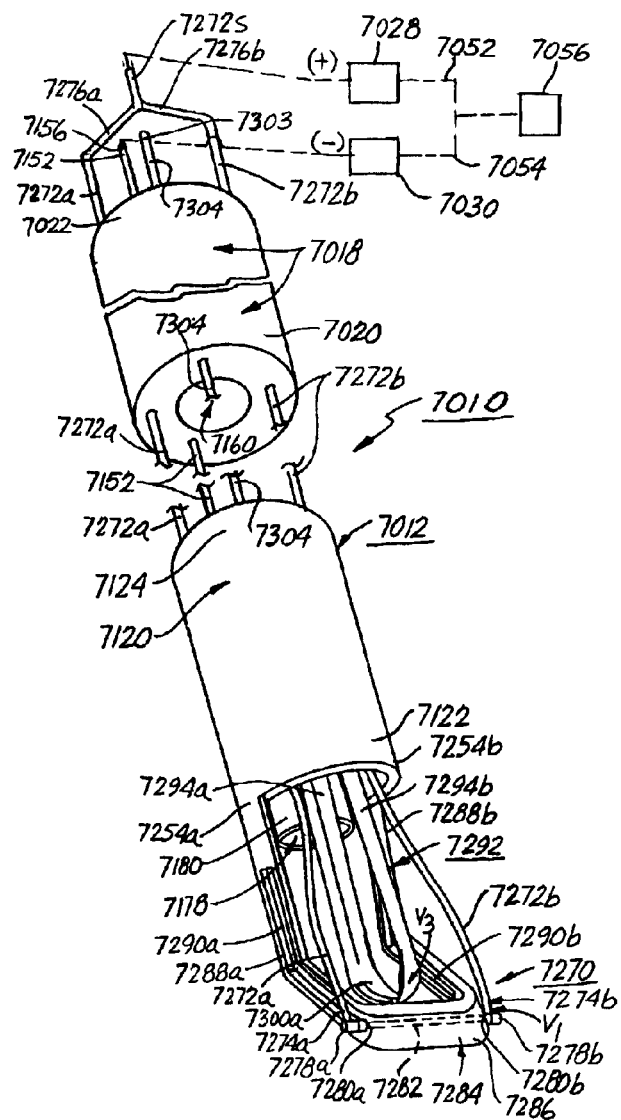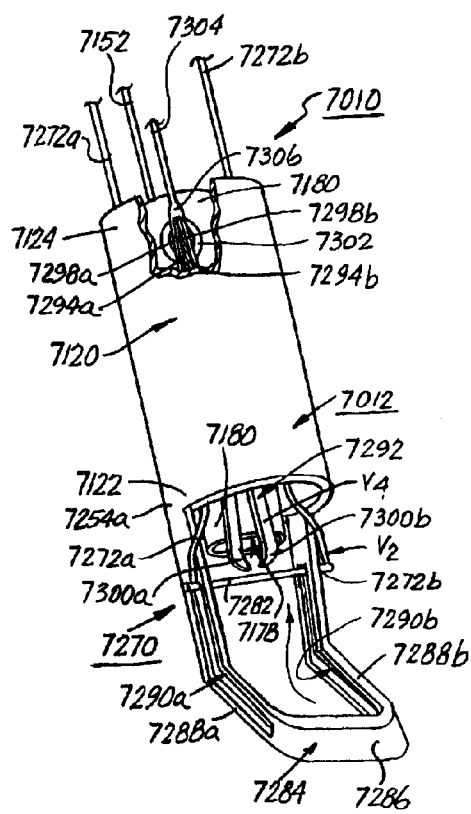
FIG. 25
FIG. 28

BIPOLAR RF EXCISION AND ASPIRATION DEVICE AND METHOD FOR ENDOMETRIOSIS REMOVAL

FIELD OF THE INVENTION

The present invention relates to a surgical biopsy instrument and method for removal of tissue from a specific area on or within a patient's body parts or organs. More particularly, the surgical biopsy instrument uses RF energy to excise the affected tissue from the patient.

BACKGROUND OF THE INVENTION

Many surgical biopsy tools and devices exist that are used to surgically remove a diseased portion of tissue, such as the surgical treatment of endometriosis by excision, vaporization or coagulation. However, none of these surgical devices were truly designed for this endometriosis procedure and their surgical use by a physician is highly skill dependent. Many laparoscopic surgeons feel that excision of the endometriosis offers the best clinical outcome and allows for pathological analysis of the affected tissue. Other medical practitioners are hesitant to excise endometriosis when it is located on sensitive organs, such as the ovaries, bladder or bowel. Further, existing surgical devices do not provide optimal control and safety.

There remains a need for a novel surgical biopsy device that uses bipolar RF energy to excise the affected tissue and uses vacuum to aspirate the excised tissue within the same biopsy device. This device would control the exact amount of tissue excised with each activation. Further, the positive (+) and negative (−) electrode configuration would result in minimal thermal damage to the unaffected, underlying tissue, permitting the physician to assess whether the diseased tissue has been completely removed. Further, the surgical device would include collection means for the excised tissue to facilitate pathological examination.

DESCRIPTION OF THE RELATED ART

Surgical biopsy and ablation devices of various designs, structures, styles and materials of construction have been disclosed in the prior art. For example, U.S. Pat. No. 5,437,665 to Munro discloses an electrosurgical loop electrode instrument for laparoscopic surgery. The instrument includes a housing and a shaft member having an expandable (uninsulated) wire loop therein. The wire loop permits current to flow into the patient through the exposed portion of a bridge segment of the loop. The surgeon can selectively choose the appropriate loop size for excising body tissue of a patient. The prior art loop electrode instrument does not have the ability to aspirate the excised tissue into a collection chamber; nor does it have the ability to limit the tissue removal to a pre-specified surgical level.

U.S. Pat. No. 5,526,822 to Burbank et al. discloses an apparatus for an automated biopsy and collection of soft tissue. The biopsy apparatus includes a piercing needle with a receiving port to trap tissue prior to cutting. A cutter advances into the receiving chamber and severs tissue which has prolapsed into the receiving port. The severed tissue is then removed from the receiving port without removing the apparatus from the lesion site, thus allowing for the accurate and rapid removal of an arbitrary number of core samples with only one insertion. The disclosed apparatus does not have the ability to excise the superficial tissues as the piercing needle goes into the tissue mass and a core biopsy is taken. The apparatus also does not have means for providing a hemostatic effect during excision.

U.S. Pat. No. 5,997,534 to Tu et al. discloses a medical ablation device for treating endometriosis, gingival or for reducing the mass of cellular tissue. The ablation device includes an elongated tubular element having an electrode means disposed at its distal section. The energy generating electrode means and means for generating a rotational sweeping force at the distal section of the tubular element is used to effect the heat treatment and the rotational sweeping massage therapy for the target tissue. This prior art ablation device is not an excision device. Additionally, the device does not have the ability to remove the tissue of interest, as it only ablates and leaves the tissue in situ rather than removing the tissue for pathological review.

U.S. Pat. No. 5,810,806 to Ritchart et al. discloses a tissue sampling probe for use in breast biopsies, laparoscopic surgery and lymphadenectory procedures. The probe includes a tubular body having a primary lumen for receiving a tissue sample. The tubular body includes a distal end and a proximal end. A non-rotating electrosurgical cutting element is provided at the end of the tubular body for cutting a section of tissue. The tubular body further includes vacuum means for drawing the excised tissue through the primary lumen to a tissue receptacle. The disclosed device is intended to remove a tubular segment of tissue, but is not optimized for very superficial tissue excision. The device also does not have the ability to limit the amount of tissue removed during each activation period.

In the foregoing circumstances, it is an object of the present invention to provide an excision and aspiration device that controls a pre-specified amount of tissue to be excised during each activation period.

Another object of the present invention is to provide an excision and aspiration device that includes a positive (+) and negative (−) electrode configuration which results in minimal thermal damage to the underlying tissue (not being excised), thus providing the physician with the ability to assess whether the diseased/affected tissue has been completely removed.

A further object of the present invention is to provide an excision and aspiration device that includes a collection means and a storage reservoir for the excised and aspirated tissue in order to facilitate the pathological examination of the diseased/affected tissue.

SUMMARY OF THE INVENTION

In accordance with the present invention, there is provided an excision and aspiration apparatus adapted to sample a tissue mass. The excision and aspiration apparatus includes receiving means for receiving a superficial portion of the total tissue mass. The excision and aspiration apparatus also includes excising means for excising the superficial portion of the tissue mass, as well as collection means for collecting the excised superficial portion of the tissue mass. Suction means, such as an external vacuum source, creates suction sufficient to draw the excised superficial portion of the tissue mass into the collection means.

BRIEF DESCRIPTION OF THE DRAWINGS

Further objects, features and advantages of the present invention will become apparent upon consideration of the following detailed description of various exemplary embodiments considered in connection with the accompanying drawings, in which:

FIG. 2 is an enlarged front perspective view of a portion of the bipolar RF excision device of FIG. 1;

FIG. 3 is an enlarged rear perspective view of the portion of the bipolar RF excision device shown in FIG. 2;

FIG. 4 is a front perspective view of a suction cup member which constitutes another aspect of the present invention, the suction cup member being adapted for use with the bipolar RF excision device of FIGS. 1;

FIGS. 5a to 5d are schematic representations which illustrate the steps involved in a method of excising and aspirating a portion of tissue using the bipolar RF excision device of FIG. 1;

FIG. 6 is a perspective view of a bipolar RF excision device constructed in accordance with a second exemplary embodiment of the present invention;

FIG. 7 is a side elevational view of the bipolar RF excision device of FIG. 6 showing a collection assembly in an extended configuration;

FIG. 15 is a perspective view of a bipolar RF excision device constructed in accordance with a fourth exemplary embodiment of the present invention;

FIG. 16 is a side elevational view of the bipolar RF excision device of FIG. 15 showing a clamping position for a pair of cutting blades;

FIG. 17 is a perspective view of the bipolar RF excision device of FIG. 15 showing the cutting blades in a retracted position;

FIG. 18 is a perspective view of a bipolar RF excision device constructed in accordance with a fifth exemplary embodiment of the present invention;

FIG. 19 is a perspective view of the bipolar RF excision device of FIG. 18 showing a collection assembly in a fully extended position;

FIG. 20a is a perspective view of the bipolar RF excision device of FIG. 19 showing a cutting blade in partial rotation;

FIG. 20b is a perspective view of the bipolar RF excision device of FIG. 20a showing the cutting blade in full rotation;

FIG. 21 is a perspective view of a bipolar RF excision device constructed in accordance with a sixth exemplary embodiment of the present invention;

FIG. 22a is a perspective view of the bipolar RF excision device of FIG. 21 showing a pair of cutting wire loops in an opened position;

FIG. 22b is a perspective view of the bipolar RF excision device of FIG. 21 showing the cutting wire loops in a tissue locating position;

FIG. 22c is a perspective view of the bipolar RF excision device of FIG. 21 showing the cutting wire loops in a closed position;

FIG. 23 is a perspective view of a bipolar RF excision device constructed in accordance with a seventh exemplary embodiment of the present invention;

FIG. 24a is a perspective view of the bipolar RF excision device of FIG. 23 showing a rotatable, cutting wire loop in a fully extended position;

FIG. 24b is a perspective view of the bipolar RF excision device of FIG. 24a showing the wire loop in a retracted position for a final tissue cut;

FIG. 25 is a perspective view of a bipolar RF excision device constructed in accordance with a ninth exemplary embodiment of the present invention;

FIG. 28 is a perspective view of the bipolar RF excision device of FIG. 28 showing the cutting wire loop and the tissue grasper in a retracted position.

DETAILED DESCRIPTION OF THE EXEMPLARY EMBODIMENTS

Figure 1:
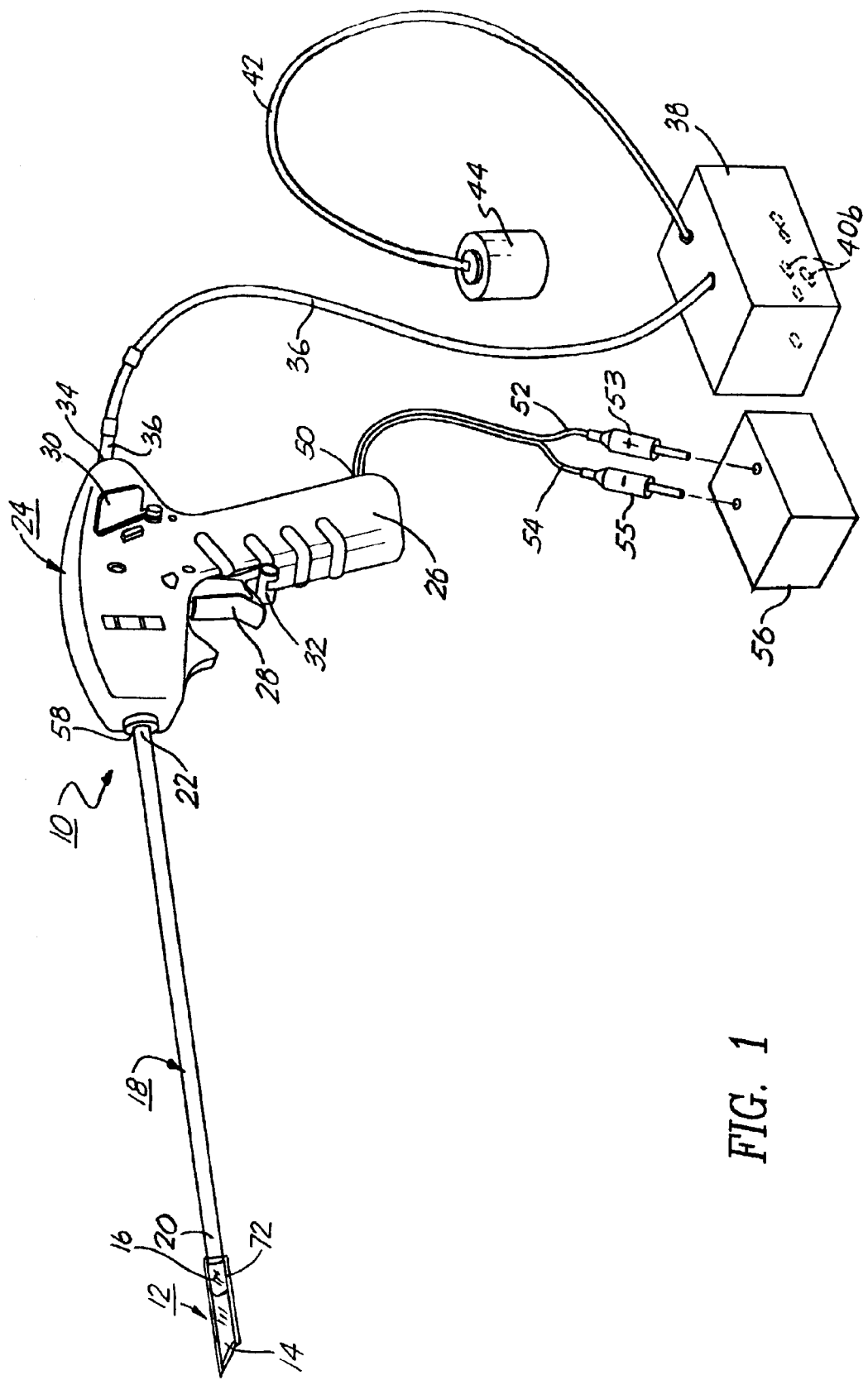
FIG. 1 is a front perspective view of a bipolar RF excision device constructed in accordance with a first exemplary embodiment of the present invention.
Figure 8:
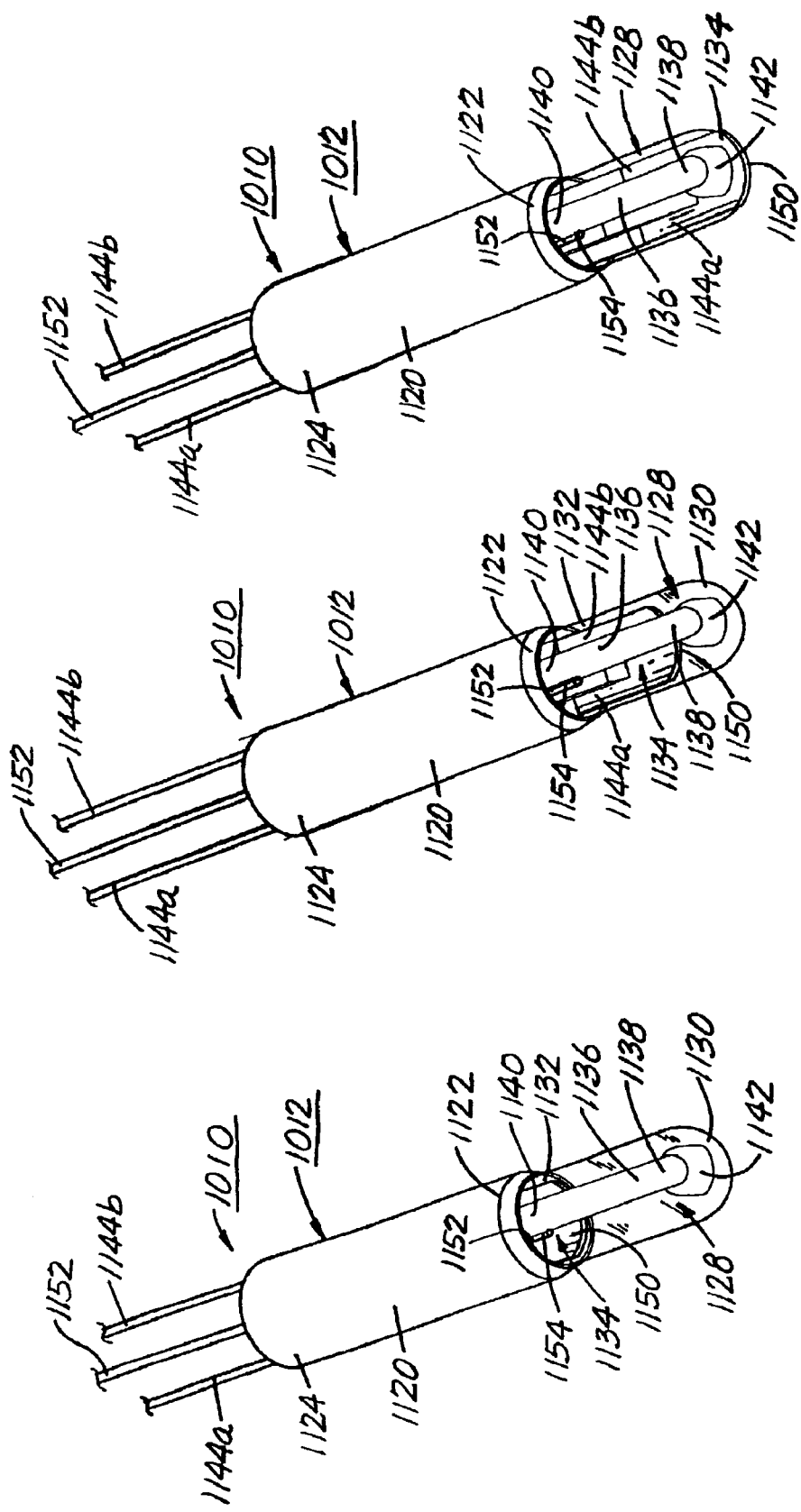
FIG. 8a is a perspective view of the bipolar RF excision device of FIG. 6 showing the collection assembly in an opened state with a cutting blade in a retracted position.
FIG. 8b is a perspective view of the bipolar RF excision device of FIG. 8a showing the cutting blade moving forward.
FIG. 8c is a perspective view of the bipolar RF excision device of FIG. 8b showing the cutting blade in its fully extended position.

Referring to FIGS. 1–5d, there is shown a bipolar RF (radio frequency) excision and aspiration device 10 for use in the surgical treatment of endometriosis. The excision device 10 includes an excision and aspiration assembly 12 having a distal end 14 and a proximal end 16, an outer tubular shaft 18 having a distal end 20 and a proximal end 22 and a handpiece housing 24 attached thereto. The handpiece housing 24 includes a handle grip 26, a finger trigger 28 for activating a cutting mechanism (to be discussed hereinafter), a thumb trigger 30 for activating an aspiration mechanism (to be discussed hereinafter) and a trigger lock 32. The housing 24 also includes a first opening 34 for receiving a first vacuum tubing 36 therein. The first vacuum tubing 36 is connected to a tissue collection chamber 38 for temporarily storing excised pieces 40b of tissue material 40. The tissue collection chamber 38 is connected to a second vacuum tubing 42, wherein vacuum tubing 42 is connected to a vacuum source 44. The housing 24 further includes a second opening 50 for receiving a positive electrode wire 52 and a negative electrode wire 54 therein. The positive and negative electrode wires 52, 54 are connected to an RF generator 56 by positive and negative electrode connectors 53, 55, respectively. Additionally, the housing 24 includes a third opening 58 for receiving the proximal end 22 of the outer tubular shaft 18. A vacuum channel opening 60 and a plurality of lumens 62, 64a and 64b run through the length of shaft 18 (see FIGS. 2 and 3).

Referring now to FIGS. 1–3, the distal end 14 of the excision and aspiration assembly 12 includes an assembly housing 66 having an outer cylindrically-shaped wall 68 and a beveled wall 70. The assembly 12 also includes an outer plastic tubing 72 for connecting and sealing the proximal end 16 of assembly 12 to the distal end 20 of tubular shaft 18 in order to provide a vacuum seal for the excision and aspiration assembly 12. The assembly housing 66 includes a vacuum channel opening 74 and a plurality of lumens 76, 78a and 78b running the length of assembly 12. The vacuum channel opening 74 and lumens 76, 78a and 78b of housing 66 are aligned with the channel opening 60 and lumens 62, 64a and 64b of tubular shaft 18, when in the assembled configuration depicted in FIGS. 1 and 3.

As shown in FIGS. 4, 5a and 5d, the excision and aspiration assembly 12 also includes a suction cup member 80, a pivot pin 82 and a rotation cable 84 for rotating the suction cup member 80 in a 90° arc. The suction cup member 80 (see FIG. 4) is substantially cylindrically-shaped and includes a flat rear wall 86, a concave cavity 88 and a circumferential perimeter wall 90. The suction cup member 80 also includes a centrally located suction opening 92 for allowing vacuum to pull a portion of tissue 40 (prior to cutting it) into the concave cavity 88 (see FIG. 5a). The perimeter wall 90 includes a pivot pin tab 93 having a pivot pin opening 94 and a rotation cable opening 96 therein. The pivot pin 82 includes a first end 98 and a second end 100. The rotation cable 84 includes a distal end 102 and a proximal end 104. The distal end 102 of rotation cable 84 is received within the rotation cable opening 96 for rotating the suction cup member 80 (see FIGS. 4, 5a and 5d). The suction cup member 80 rotates from a vacuuming position $V_1$ allowing the vacuum to pull a portion of tissue 40 into the concave cavity 88 of the suction cup member 80 prior to cutting it (the tissue material) to a tissue removal position $V_2$ which allows the vacuum to draw the excised tissue 40b into the vacuum channel opening 74 after cutting. Further, the rotational cable 84 extends through the length of lumens 76, 62 of housing 66 and shaft 18, respectively, such that the proximal end 104 of the rotational cable 84 is attached to the thumb trigger 30 for activating the suction cup member 80 from the vacuuming position $V_1$ to the tissue removal position $V_2$. Additionally, the rotational cable 84 and the suction cup member 80 also function as the return negative electrode for the bipolar RF excision device 10, wherein the proximal end 104 of rotational cable 84 is attached to the negative electrode wire 54.

Referring again to FIGS. 1–5d, the excision and aspiration assembly 12 further includes an actuation cable 110 having a distal end 112 and a proximal end 114. The distal end 112 of actuation cable 110 includes a cutting section 116 and a pair of return actuation cable arms 118a and 118b integrally attached to the cutting section 116 as shown in FIGS. 5a and 5d. The cutting section 116 (see FIG. 5d) has a width approximately in the range of 2.25 mm to 2.50 mm. The return actuation cable arms 118a, 118b extend through the length of lumens 78a, 64a and 78b, 64b of assembly housing 66 (see FIGS. 2 and 3) and shaft 18, respectively, such that the proximal end 114 of the actuation cable arms 118a, 118b (cable arms 118a, 118b are twisted together at the proximal end 114) are attached to the finger trigger 28 for actuating the cutting section 116, in a retracting motion relative to the transverse axis of the vacuum channel opening 74, in order to cut a portion of tissue material 40. Additionally, the cutting section 116 of the actuation cable 110 also functions as the positive electrode for the bipolar RF excision device 10, wherein the proximal end 114 of actuation cable 110 is also attached to the positive electrode wire 52.

In operation, the bipolar RF excision and aspiration device 10 operates in the following manner when excising and aspirating a portion of tissue 40 for endometriosis removal. With reference to FIG. 5a, the medical practitioner places the beveled wall 70 of the device 10 in contact with the affected tissue 40, such that the beveled wall 70 is in a flat, longitudinal relationship with the tissue 40 in order to form a vacuum seal therewith. With the suction cup member 80 in its vacuum position $V_1$, the vacuum is then activated (by an external mechanism) to pull a portion of the tissue 40 into the concave cavity 88 via the suction opening 92 of the suction cup member 80 such that it abuts the cutting section 116 in preparation of cutting the abutted tissue 40 by the RF energy created between the cutting section 116 of actuation cable 110 (the positive electrode) and the suction cup member 80 (the negative electrode). The RF energy created between the positive and negative electrodes allows the cutting of the tissue 40 to proceed smoothly.

Referring now to FIG. 5b, the operator next depresses the finger trigger 28 (see FIG. 1) which in turn activates the cutting section 116 in a retracting motion relative to the transverse axis of the vacuum channel opening 74, wherein the cutting section 116 is made to cut a small piece 48b of tissue 48 from the patient's affected area. Each of the actuation arms 118a, 118b retracts a small distance within lumens 78a, 64a and 78b, 64b via the finger trigger 28. As shown in FIG. 5c, the cutting section 116 of the actuation cable 110 completes its pass along the opening 74 of the beveled wall 70 in order to completely sever the small piece 40b of tissue 40.

With reference to FIG. 5d, after removing the device 10 from the tissue surface, the operator now releases the finger trigger 28 which automatically returns the cutting section 116 of actuation cable 110 to its start position by the use of a contracting spring (not shown) connected to the finger trigger 28 (see FIG. 1). The operator now depresses the thumb trigger 30 thereby causing the suction cup member 80 to move from the vacuum position $V_1$ to the tissue aspiration position $V_2$. The tissue aspiration position $V_2$ allows the vacuum to pull the excised tissue piece 40b into the vacuum channel openings 74, 60, respectively, after cutting. The excised tissue piece 40b then passes through the first vacuum tubing 36 (from channel opening 60) to the tissue collection reservoir 38 (see FIG. 1), where it is temporarily stored. After the operator releases the thumb trigger 30, the suction cup member 80 rotates automatically back (a 90° arc rotation) to its starting vacuum position $V_1$, as depicted in FIG. 5a. In an alternate mode of operation, the tissue piece 40b aspiration could be done prior to returning the cutting section 116 to its start position.

Alternatively, the distance between the suction cup member 80 and the cutting section 116 can be varied or adjusted to allow different volumes of tissue 40 to be excised. In addition, the size (i.e., diameter) of the vacuum channel opening 74 can be selectively adjusted or varied to change the "footprint" (i.e., area) of the tissue 40 to be excised. Thus, the device 10 provides for the safe removal of a precise amount of superficial (i.e., surface) tissue 40. In the case of endometriosis, the desired depth of the excision is typically in a range of from about 0.5 mm to about 5.0 mm. Further, this device 10 can be used with either vascular tissue (i.e., blood vessels running through the tissue) or avascular tissue (i.e., a lack of blood vessels running through the tissue), as this device 10 is designed to only remove a specific amount of superficial tissue with each activation, allowing minimal thermal damage to the unaffected, underlying tissue.

A second exemplary embodiment of the present invention is illustrated in FIGS. 6 to 8c. Elements illustrated in FIGS. 6 to 8c which correspond to the elements described above with reference to FIGS. 1 to 5d have been designated by corresponding reference numbers increased by one thousand. The second embodiment is constructed and operates in the same manner as the first embodiment, unless it is otherwise stated.

With reference to FIGS. 6 to 8c, a bipolar excision and aspiration device 1010 includes an excision and aspiration assembly 1012 having an outer tube 1120 which is provided with a distal end 1122 and a proximal end 1124. The outer tube 1120 is also provided with a channel 1126 for receiving a movable, inverted U-shaped canopy member 1128 having a distal end 1130 and a proximal end 1132. The assembly 1012 further includes a cutting blade 1134 movable from a retracted position $P_1$ to an extended position $P_2$, and a movable suction (vacuum) tube 1136 having a distal end 1138 and a proximal end 1140. The distal end 1138 of suction tube 1136 includes an integral suction cup member 1142. The cutting blade 1134 includes a pair of return actuation cable arms 1144a and 1144b having distal ends 1146a, 1146b and a proximal end 1148. The distal ends 1146a, 1146b of actuation cable arms 1144a, 1144b are integrally attached to the cutting blade 1134. The cutting blade 1134 further includes a front cutting edge 1150 for cutting a small portion of tissue (not shown) via the RF bipolar energy field generated by the positive (+) electrode (the cutting blade 1134) and negative (−) electrode (the suction cup member 1142). The assembly 1012 also includes an extension cable 1152 having a distal end 1154 and a proximal end 1156. The canopy member 1128 and suction tube 1136 extend and retract relative to each other, as the proximal ends 1132, 1140 of the canopy member 1128 and suction tube 1136, respectively, are co-jointly attached to the extension cable 1152 at its distal end 1154. The extension cable 1152 at its distal end 1154 becomes the negative return electrode (−) for attachment to the negative electrode wire (−) 1054 of RF generator 1056.

In operation, the bipolar RF excision and aspiration device 1010 operates in the following manner, as referenced in FIGS. 8a to 8c which illustrate the steps involved in a method of excising and aspirating a portion of tissue (not shown) for removal by device 1010. With reference to FIG. 8a, the medical practitioner actuates device 1010 which outwardly moves and extends the canopy member 1128 and suction tube 1136 via the extension cable 1152, such that the suction cup member 1142 on suction tube 1136 is then placed in contact with the affected tissue matter (not shown). After the suction cup member 1142 forms a vacuum seal with the tissue to be excised and aspirated, a small portion of the tissue is pulled into the suction cup member 1142 in preparation for a cutting operation to be performed by the RF energy between the cutting blade 1134, which functions as the positive (+) electrode, and the suction cup member 1142, which functions as the return negative (−) electrode. The RF energy between the positive and negative electrodes allows the cutting of the tissue to proceed smoothly and efficiently.

Referring now to FIG. 8b, the medical practitioner now depresses the finger trigger 1028 which in turn causes the cutting blade 1134 to extend from its retracted position $P_1$ to its extended position $P_2$ relative to a longitudinal axis along the length of the suction tube 1136. During such movement of the cutting blade 1134, its cutting edge 1150 cuts (via the RF energy field) a small portion of tissue from the patient's affected area (see FIG. 8b).

As shown in FIG. 8c, the cutting blade 1134 completes its pass along the small portion of tissue, thereby severing the aforementioned excised portion of tissue from the patient. After removing the device 1010 from the tissue surface, the medical practitioner now releases the finger trigger 1028 which automatically returns the cutting blade 1134 to its retracted position $P_1$ via actuator cable arms 1144a, 1144b, as shown in FIG. 6. This retraction is accomplished by the use of a contracting spring (not shown) connected to the finger trigger 1028 (see FIG. 6). The suction cup member 1142 pulls the excised tissue into the vacuum tube 1136, from where it is delivered to the tissue collection reservoir (not shown).

A third exemplary embodiment of the present invention is illustrated in FIGS. 9 to 14b. Elements illustrated in FIGS. 9 to 14b which correspond to the elements described above with reference to FIGS. 6 to 8c have been designated by corresponding reference numbers increased by one thousand. The third embodiment is constructed and operates in the same manner as the second embodiment 1010, unless it is otherwise stated.

Figures 11A, 11B:
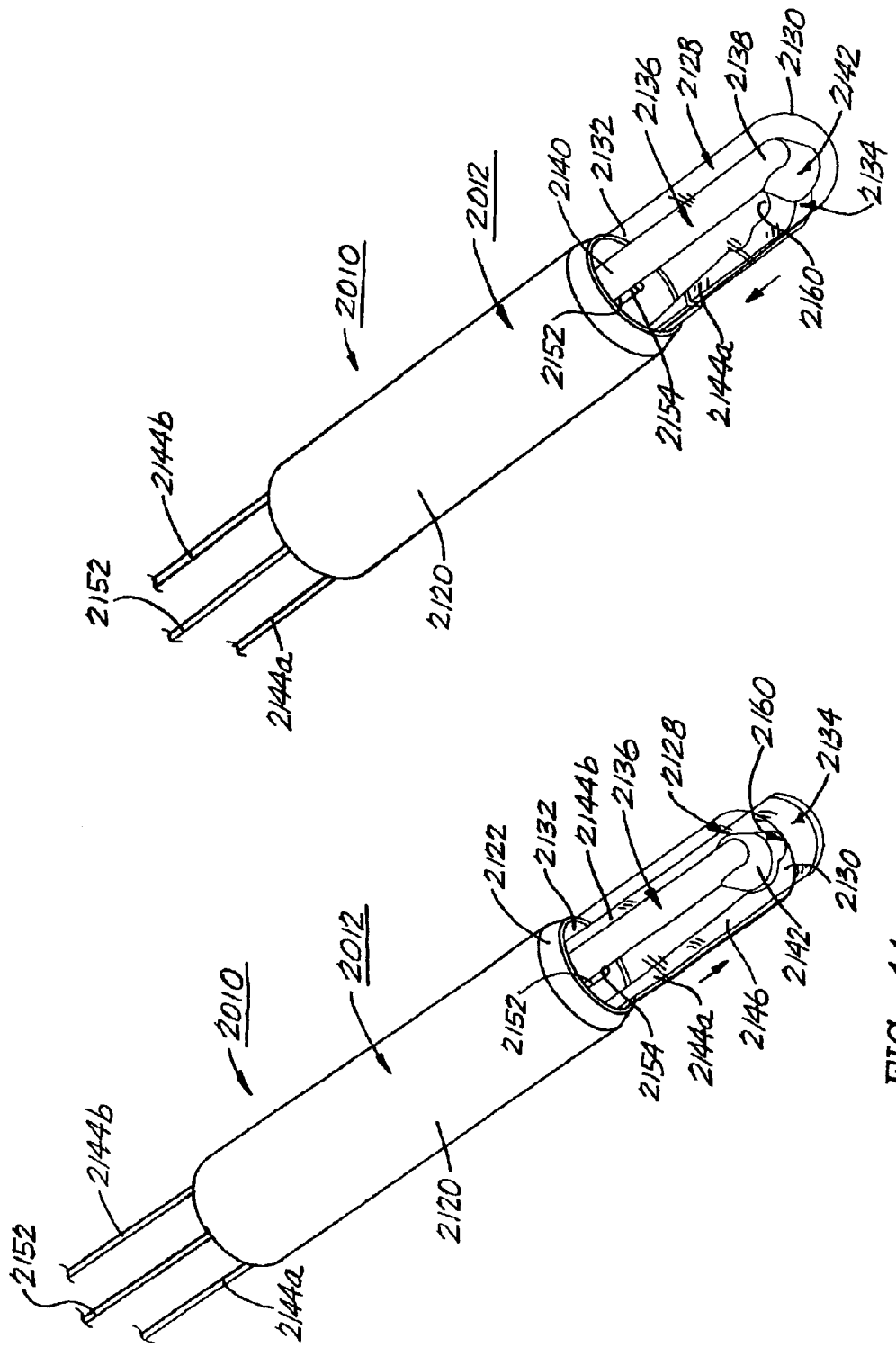
FIG. 11a is a perspective view of the bipolar RF excision device of FIG. 9 showing the collection assembly with a cutting blade in a fully extended position.
FIG. 11b is a perspective view of the bipolar RF excision device of FIG. 11a showing the cutting blade moving rearward for a complete cut.
Figure 12A:
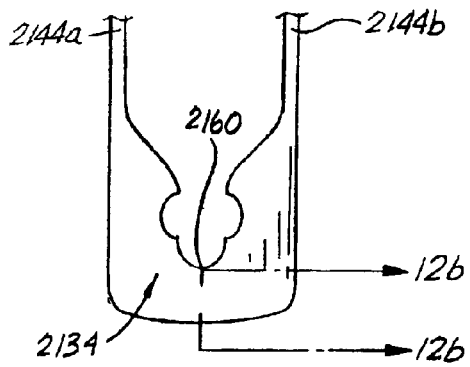
FIG. 12a is a top plan view of the cutting blade of FIG. 11a, without the suction cup member and suction tube being shown.
Figure 12B:
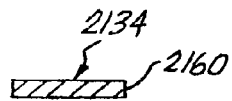
FIG. 12b is a cross-sectional view of the cutting blade of FIG. 12a, the cross-section being taken along section line 12b—12b and looking in the direction of the arrows.

With reference to FIGS. 9 to 11b, a bipolar excision and aspiration device 2010 includes an excision and aspiration assembly 2012, having a cutting blade 2134 which is movable from an extended position $R_1$ to a retracted position $R_2$. The cutting blade 2134 includes a rear, inner cutting edge 2160 for cutting a small portion of tissue (not shown) via the RF bipolar energy field generated by the position (+) electrode (cutting blade 2134) and the negative (−) electrode (suction cup member 2142). As shown in FIGS. 12a and 12b, the cutting blade 2134 has a substantially rectangular cross-sectional shape. All of the remaining component parts are exactly the same as the second exemplary embodiment 1010 of the present invention.

Figure 13A:
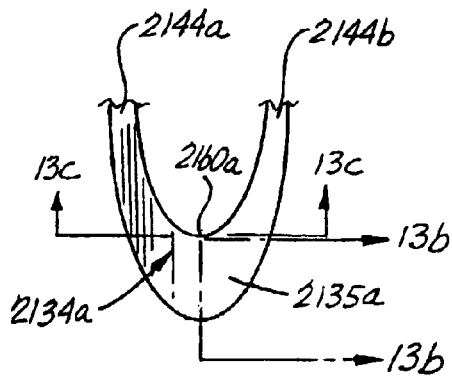
FIG. 13a is a top plan view of an alternate cutting blade, without the suction cup member and suction tube being shown.
Figure 13B:
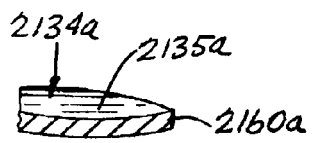
FIG. 13b is a cross-sectional view of the cutting blade of FIG. 13a, the cross section being taken along section line 13b—13b and looking in the direction of the arrows.
Figure 13C:
FIG. 13c is a cross-sectional view of the cutting blade of FIG. 13a, the cross section taken along section line 13c—13c and looking in the direction of the arrows.

With reference to FIGS. 13a to 13c, there is shown an alternate arrangement for a cutting blade 2134a having a substantially concave, U-shaped configuration (see FIG. 13a). The cutting blade 2134a, as depicted in FIG. 13c, has a substantially concave surface 2135a. The cutting blade 2134a works exactly like cutting blade 2134 except that the concave surface 2135a of blade 2134a interfits with a concave inner surface 2162 of channel 2126 of the outer tube 2120.

Figure 14A:
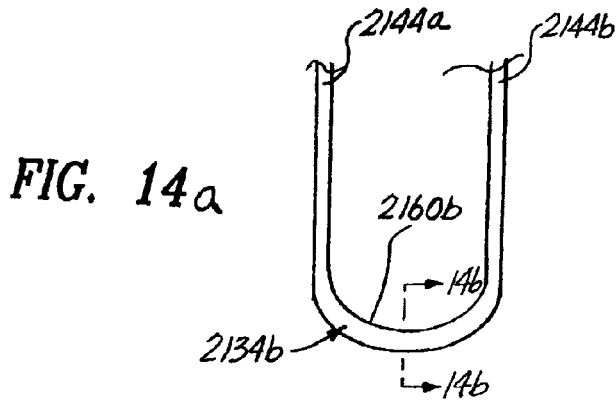
FIG. 14a is a top plan view of yet another alternate cutting blade, without the suction cup member and suction tube being shown.
Figure 14B:
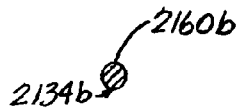
FIG. 14b is a cross-sectional view of the cutting blade of FIG. 14a, the cross section being taken along section line 14b—14b and looking in the direction of the arrows.

Referring now to FIGS. 14a and 14b, there is shown yet another alternate arrangement for a cutting blade 2134b having a substantially U-shaped configuration. The cutting blade 2134b, as shown in FIG. 14b, has a substantially circular cross-sectional shape. The cutting blade 2134b works exactly like cutting blade 2134 during its cutting movement.

In operation, the bipolar RF excision and aspiration device 2010 operates in the following manner, as referenced in FIGS. 11a and 11b which illustrate the steps involved in a method of excising and aspirating a small portion of tissue (not shown) for removal by device 2010. With reference to FIG. 11a, the canopy member 2128 and suction tube 2136 outwardly move and extend themselves via the extension cable 2152 with the actuation of device 2010. Simultaneously, the cutting blade 2134 is also actuated from a retracted position $R_1$ to an extended position $R_2$ relative to a longitudinal axis of the suction tube 2136, such that the cutting blade 2134 extends beyond the distal end 2130 of the canopy member 2128 (see FIG. 11a) in preparation for excising a small portion of the affected tissue.

Referring now to FIG. 11a, the practitioner now places the device 2010 over the tissue to be excised, whereupon the suction tube 2136 contacts the affected tissue (not shown) and the suction cup member 2142 forms a vacuum seal with the tissue that is to be excised and aspirated. A small portion of tissue is then pulled into the suction cup member 2142 in preparation for a cutting operation performed by the RF energy between the positive (+) and negative (−) electrodes 2134 and 2142, respectively. The finger trigger 2028 is then depressed to actuate the cutting blade 2134 in order to sever a portion of tissue within the suction cup member 2142 such that the cutting blade 2134 begins to retract to its retracted position $R_1$ from its extended position $R_2$. During such movement of the cutting blade 2134, its inner cutting edge 2160 cuts (via the RF energy field) a small portion of tissue from the patient's affected area (see FIG. 11b).

Figure 9:
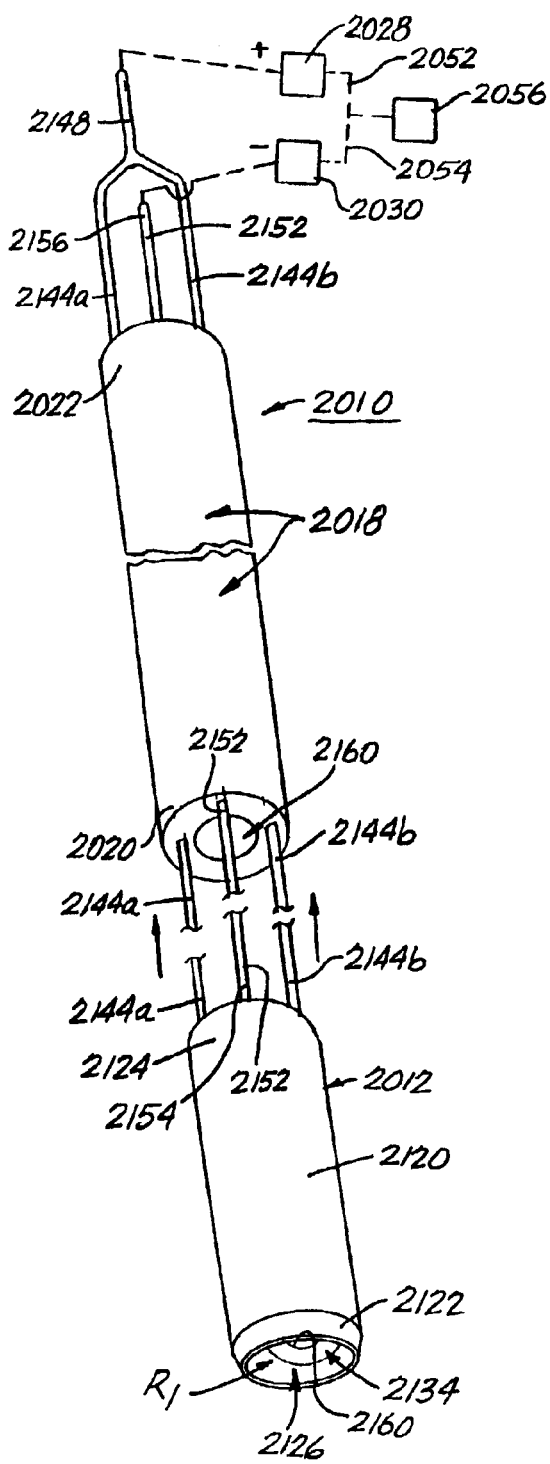
FIG. 9 is a perspective view of a bipolar RF excision device constructed in accordance with a third exemplary embodiment of the present invention.
Figure 10:
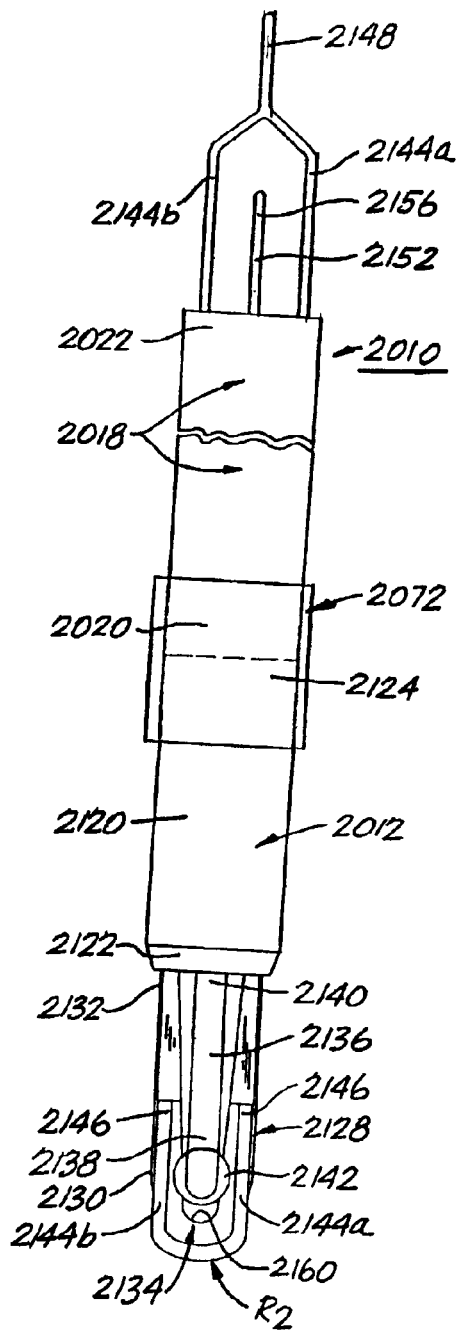
FIG. 10 is a side elevational view of the bipolar RF excision device of FIG. 9 showing a collection assembly in an extended configuration.

Referring now to FIG. 11b, the cutting blade 2134 completes its pass along the small portion of tissue, thereby severing the aforementioned excised portion of tissue from the patient. After removing the device 2010 from the tissue surface, the practitioner next releases the finger trigger 1028 which automatically returns the cutting blade 2134 to its retracted position $R_1$ via actuator cable arms 2144a, 2144b, whereupon the suction tube 2136 and canopy member 2128 also retracts to its start position, as shown in FIG. 9, via the extension cable 2152. The suction cup member 2142 pulls the excised tissue into the suction tube 2136, from where it is delivered to the tissue collection reservoir (not shown).

A fourth exemplary embodiment of the present invention is illustrated in FIGS. 15 to 17. Elements illustrated in FIGS. 15 to 17 which correspond to the elements described above with reference to FIGS. 6 to 8c have been designated by corresponding reference numbers increased by two thousand. The fourth embodiment is constructed and operates in the same manner as the second embodiment 1010, unless it is otherwise stated.

With reference to FIGS. 15 to 17, a bipolar excision and aspiration device 3010 includes an excision and aspiration assembly 3012 having a cutting assembly 3170 which is movable from an extended position $Q_1$ to a retracted position $Q_2$. The cutting assembly 3170 includes a pair of cutting arms 3172a, 3172b, each having an inner cutting edge 3174a, 3174b thereon. The cutting arms 3172a, 3172b are integrally connected to a return actuation cable arm 3176a, 3176b, respectively, as depicted in FIG. 15. In turn, actuation cable arms 3176a, 3176b are integrally connected to the cable arms 3144a, 3144b, respectively, of excision assembly 3012 (see FIGS. 15 and 16). The cutting arms 3172a, 3172b act as claspers to hold a small portion of tissue in close proximity to a suction tube opening 3178 of a suction tube 3180, which has a distal end 3182 and a proximal end 3184. The distal end 3182 of suction tube 3180 is adjacent to tube opening 3178. The proximal end 3184 of suction tube 3180 is connected to the distal end 3154 of extension cable 3152 for extending and retracting of the suction tube 3180 from its extended position $Q_1$, to its retracted position $Q_2$ (see FIGS. 16 and 17).

In operation, the bipolar RF excision and aspiration device 3010 operates in the following manner, as referenced in FIGS. 15 to 17 which illustrate the steps involved in a method of excising and aspirating a small portion of tissue (not shown) for removal by device 3010. Upon actuation of device 3010, the cutting assembly 3170 and the suction tube 3180 are extended to the extended position $Q_1$ from their retracted position $Q_2$ (see FIGS. 15 to 17), such that the inner cutting edges 3174a, 3174b are adjacent to the distal end 3182 of the suction tube opening 3178 in preparation for excising a small portion of the affected tissue.

Referring now to FIGS. 15 and 16, the medical practitioner next places the device 3010 over the targeted tissue such that the suction tube opening 3178 of suction tube 3180 contacts the affected tissue (not shown) and the suction tube opening 3178 forms a vacuum seal with the small portion of tissue that is to be excised and aspirated. A small portion of the tissue is then pulled into the suction tube opening 3178 of suction tube 3180 in preparation for a cutting operation performed by RF energy between the positive (+) and negative (−) electrodes 3170 and 3180, respectively. The finger trigger 3028 is then depressed to actuate the cutting assembly 3170 in order to sever the portion of tissue being held within the suction tube opening 3178. During such movement of the cutting arms 3172a, 3172b, its inner cutting edges 3174a, 3174b (being in their extended position $Q_1$) cut a small portion of tissue matter (via the RF energy field) from the patient's affected area. The inner cutting edges 3174a, 3174b move inwardly (see FIGS. 16 and 17) to sever the tissue matter, as the cutting assembly 3170 and the suction tube 3180 retracts to its start position $Q_2$.

Referring now to FIG. 17, the inner cutting edges 3174a, 3174b of cutting assembly 3170 complete their pass along the small portion of tissue, thereby severing the aforementioned excised portion of tissue from the patient. After removing the device 3010 from the tissue surface, the medical practitioner now releases the finger trigger 3028 which automatically returns the cutting assembly 3170 and the suction tube 3180 to the retracted position $Q_2$ (see FIG. 17) via actuator cable arms 3144a, 3144b and extension cable 3152, respectively. The suction tube 3180 then draws the excised tissue into the suction tube 3180 from tube opening 3178, whereupon the excised tissue is delivered to the tissue collection reservoir (not shown).

A fifth exemplary embodiment of the present invention is illustrated in FIGS. 18 to 20b. Elements illustrated in FIGS. 18 to 20b which correspond to the elements described above with reference to FIGS. 6 to 8c have been designated by corresponding reference numbers increased by three thousand. The fifth embodiment is constructed and operates in the same manner as the second embodiment 1010 unless it is otherwise stated.

With reference to FIGS. 18 to 20b, a bipolar excision and aspiration device 4010 includes and excision and aspiration assembly 4012 having a concave-shaped rotatable cutting blade 4190 which is movable from a retracted position $S_1$ to an extended position $S_2$ The rotatable cutting blade 4190 includes a distal blade tip 4192 having a substantially concave-shape. The concave-shaped blade tip 4192 partially encases a portion 4142a of the suction cup member 4142 of suction tube 4136 (see FIG. 20b). The concave-shaped blade tip 4192 includes an inner cutting edge 4194 for cutting a small portion of tissue (not shown) via the RF bipolar energy field generated by the positive (+) electrode (the blade tip 4192) and negative (−) electrode (the suction cup member 4142), respectively. The cutting blade 4190 configures and interfits with the canopy member 4128, when the canopy member 4128 and suction tube 4136 are in an extended state $S_2$ (see FIG. 19). The inner cutting edge 4194 of cutting blade 4190 rotates in a clockwise manner $M_1$ in order to excise the small portion of tissue within the suction cup member 4142, and then rotates back in a counter-clockwise manner $M_2$ after the completion of the cutting of the excised tissue within the suction cup member 4142. The canopy member 4128 and suction tube 4136 extend from and retract relative to each other, as the proximal ends 4132, 4140 of the canopy member 4128 and suction tube 4136, respectively, are co-jointly attached to the extension cable 4152 at its distal end 4154. The extension cable 4152 becomes the negative (−) electrode for attachment to the negative electrode wire (−) 4054 of RF generator 4056.

In operation, the bipolar RF excision and aspiration device 4010 operates in the following manner, as referenced in FIGS. 18 to 20b, which illustrate the steps involved in a method of excising and aspirating a portion of tissue (not shown) for removal by device 4010. With reference to FIGS. 18 and 19, the medical practitioner actuates device 4010 which outwardly moves and extends the canopy member 4128 and suction tube 4136 via the extension cable 4152, such that the suction cup member 4142 on suction tube 4136 is then placed in contact with the affected tissue (not shown). The suction cup member 4142 then forms a vacuum seal with the tissue to be excised and aspirated such that small portion of the tissue matter is pulled into the suction cup member 4142 in preparation for a cutting operation performed by the RF energy between the blade tip 4192, which functions as the positive (+) electrode, and the suction cup member 4142, which functions as the return negative (−) electrode. The concave-shaped cutting blade 4190 is now extended from a retracted position $S_1$ to an extended position $S_2$ relative to a longitudinal axis along the length of the canopy member 4128 and suction tube 4136, respectively. The RF energy between the positive and negative electrodes allows the cutting and excising of the tissue to proceed smoothly and efficiently.

Referring now to FIGS. 18 and 20a, the medical practitioner now depresses the finger trigger 4028 which in turn causes the cutting blade 4190 to rotate in a clockwise motion $M_1$ about the outer surface of the canopy member 4128. During such movement of the cutting blade 4190, its inner cutting edge 4194 cuts (via the RF energy field) a small portion of tissue material from the patient's affected area.

As shown in FIG. 20b, the inner cutting edge 4194 of cutting blade 4190 completes its pass along the small portion of tissue, thereby severing the aforementioned excised portion of tissue from the patient. After removing the device 4010 from the tissue surface, the medical practitioner now releases the finger trigger 4028 which automatically returns the cutting blade 4190 to its actuation/extended position $S_2$ with the rotating of the cutting blade 4190 in a counter-clockwise motion $M_2$ about the outer surface of the canopy member 4128. This axial rotation is accomplished by the use of a rotational contracting spring (not shown) connected to the finger trigger 4028 (see FIG. 18). The suction cup member 4142 then pulls the excised tissue into the suction tube 4136, from where it is delivered to the tissue collection reservoir (not shown). With the release of the finger trigger 4028, the canopy member 4128, the suction tube 4136 and the cutting blade 4190 all retract to their start position $S_1$, as shown in FIG. 18.

A sixth exemplary embodiment of the present invention is illustrated in FIGS. 21 to 22c. Elements illustrated in FIGS. 21 to 22c which correspond to the elements described above with reference to FIGS. 6 to 8c have been designated by corresponding reference numbers increased by four thousand. The sixth embodiment is constructed in the same manner as the second embodiment 1010 unless it is otherwise stated.

With reference to FIGS. 21 to 22c, a bipolar excision and aspiration device 5010 includes an excision and aspiration assembly 5012 having a rotatable cutting assembly 5200 which is movable from a retracted position $T_1$ to an extended position $T_2$. The rotatable cutting assembly 5200 includes a pair of rotatable cutting arms 5202a, 5202b, each having a centrally located U-shaped cutting edge 5204a, 5204b thereon. Each of the cutting arms 5202a, 5202b includes a distal end 5206a, 5206b and a proximal end 5208a, 5208b, respectively, attached thereto. The distal ends 5206a, 5206b of each cutting arm 5202a, 202b include a connecting member 5210 attached thereto. The connecting member 5210 allows each of the cutting arms 5202a, 5202b to rotate independently of each other, such that the cutting arm 5202a is able to rotate in a counter-clockwise manner $M_2$ within a 180° arc, and the cutting arm 5202b is able to rotate in a clockwise manner $M_1$ within a 180° arc (see FIGS. 22a to 22c). The proximal ends 5208a, 5208b of each cutting arm 5202a, 5202b includes a connecting pin 5212a, 5212b thereon. Each of the connecting pins 5212a, 5212b are attached to the distal ends 5146a, 5146b of actuation cable arms 5144a, 5144b, respectively. The actuation cable arms 5144a, 5144b allow each of the cutting arms 5202a, 5202b to rotate independently of each other, such that the connecting pin 5212a and the cutting arm 5202a are able to rotate in a counter-clockwise manner $M_2$ for a 180° arc (½ turn) via the actuation cable arm 5144a, and the connecting pin 5212b and the cutting arm 5202b are able to rotate in a clockwise manner $M_1$ for a 180° arc (½ turn) via the actuation cable arm 5144b (see FIGS. 22a to 22c).

As shown in FIGS. 22a to 22c, the excision and aspiration assembly 5012 also includes a slidable inner sleeve 5214 having an axial opening 5216 for receiving the distal end 5182 of suction tube 5180. The inner sleeve 5214 is slidable received within channel opening 5126 of outer tube 5120. The inner sleeve 5214 and suction tube 5180 extend and retract relative to each other, as the distal end 5154 of the extension cable 5152 is attached to the slidable inner sleeve 5214. The suction tube opening 5178 of suction tube 5180 is in a proximate and adjacent position to each of the proximal ends 5208a, 5208b of cutting arms 5202a, 5202b, respectively (see FIG. 22a).

In operation, the bipolar RF excision and aspiration device 5010 operates in the following manner, as referenced in FIGS. 21 to 22c which illustrate the steps involved in a method of excising and aspirating a small portion of the affected tissue (not shown) for removal by device 5010. With reference to FIGS. 21 and 22a, the practitioner actuates device 5010 which initially extends the suction tube 5180, as well as the rotatable cutting assembly 5200, from a retracted position $T_1$ to an extended (start) position $T_2$. The initial actuation, as shown in FIG. 22b, also deploys and rotates each of the cutting arms 5202a, 5202b of cutting assembly 5200 in a 90° arc motion, such that the cutting arms 5202a, 5202b are in the same horizontal plane with each other. The cutting arms 5202a, 5202b are then placed on top of a small portion of the affected tissue in a locating and scooping position $T_3$. Once the practitioner sets the cutting arms 5202a, 5202b in this locating position $T_3$, the suction tube opening 5178 of the suction tube 5180 is then deployed to be over the affected tissue (see FIG. 22b) and the deployed cutting arms 5202a, 5202b are in position for a cutting operation performed by the RF energy between the U-shaped cutting edges 5204a, 5204b, which functions as the positive (+) electrodes, and the suction tube 5180, which functions as the return negative (−) electrode. The RF energy between the positive (+) and negative (−) electrodes allows the excising and scooping-out of the tissue to proceed smoothly and efficiently.

Referring now to FIG. 22c, the practitioner now depresses the finger trigger 5028 which in turn causes each of the cutting arms 5202a, 5202b to rotate in a 90° arc, wherein the cutting edge 5204a of cutting arm 5202a rotates in a counter-clockwise movement $M_2$ and the cutting edge 5204b of cutting arm 5204b rotates in a clockwise movement $M_1$. During such movement of the cutting arms 5202a, 5202b, their cutting edges 5204a, 5204b cut, scoop-out and excise (via the RF energy), a small portion of the affected tissue. This opposing axial rotation of the cutting arms 5202a, 5202b of cutting assembly 5200 is accomplished by the use of rotational contracting springs (not shown) connected to the finger trigger 5028 (see FIG. 21) and to the actuation cable arms 5144a, 5144b, accordingly. After removing the device 5010 from the tissue surface, the practitioner now releases the finger trigger 5028, where then the suction tube opening 5178 of suction tube 5180 pulls the excised tissue into the suction tube 5180, from where it is delivered to the tissue collection reservoir (not shown). With the release of the finger trigger 5028 (see FIG. 21), each of the cutting arms 5202a, 5202b rotate back through a 180° arc to their respective extended/start position $T_2$ (see FIG. 22a) and the suction tube 5180 and the cutting assembly 5200 jointly retract to their retracted position $T_1$, as shown in FIG. 21.

A seventh exemplary embodiment of the present invention is illustrated in FIGS. 23 to 24b. Elements illustrated in FIGS. 23 to 24b which correspond to the elements described above with reference to FIGS. 6 to 8a have been designated by corresponding reference numbers increased by five thousand. The seventh embodiment is constructed in the same manner as the second embodiment 1010 unless it is otherwise stated.

With reference to FIGS. 23 to 24b, a bipolar excision and aspiration device 6010 includes an excision and aspiration assembly 6012 having a cutting assembly 6220 which is moveable from an extended position $W_1$ to a retracted position $W_2$. The cutting assembly 6220 includes a rotating loop member 6222 having a top bar 6224, side bars 6226, 6228 and a U-shaped cutting edge 6230, all being integrally connected together. Each of the side bars 6226, 6228 of loop member 6222 include an inwardly positioned connector tab 6232a, 6232b, respectively, thereon. The rotating loop member 6222 has a circular cross-sectional shape. The cutting assembly 6220 further includes a pair of upper adjustment wires 6234a, 6234b and a pair of lower adjustment wires 6236a, 6236b. Each of the upper adjustment wires 6234a, 6234b includes a distal end 6238a, 6238b and a proximal end 6240a, 6240b, respectively. Each of the distal ends 6238a, 6238b of the upper adjustment wires 6234a, 6234b includes a connector ring 6242a, 6242b for attachment to the top bar 6224 of loop member 6222, respectively, as shown in FIG. 23. Each of the lower adjustment wires 6236a, 6236b includes a distal end 6244a, 6244b and a proximal end 6246a, 6246b, respectively. Each of the distal ends 6244a, 6244b of lower adjustment wires 6236a, 6236b includes a connector ring 6248a, 6248b for attachment to each of the connector tabs 6232a, 6232b on side bars 6226, 6228, respectively, of loop member 6222 (see FIGS. 23 and 24a). The cutting assembly 6220 also includes a pair of adjustment tracks 6250a, 6250b, each having a longitudinal channel opening 6252a, 6252b therein. Each of the adjustment tracks 6250a, 6250b are integrally connected on opposing sides 6254a, 6254b of the outer tube 6120 at its distal end 6122 (see FIG. 23). Each of the connector tabs 6232a, 6232b on side bars 6226, 6228 of loop member 6222 are received within each of the channel openings 6252a, 6252b of adjustment tracks 6250a, 6250b, respectively (see FIG. 23). The cutting edge 6230 of loop member 6222 can rotate in a 90° arc in order to select a depth of tissue to be excised by the movement of the upper and lower adjustment wires 6234a, 6236a, 6234b, 6236b. The upper and lower adjustment wires 6234a, 6236a, 6234b, and 6236b can be pushed or pulled with slight manipulations of the finger trigger 6028 in order to adjust for that aforementioned selection of a depth of tissue to be excised (to be further discussed hereinafter). It should be understood by a person skilled in the art that other adjusting mechanisms can be employed to control the angle of the loop member 6222. For example, more or less adjustment wires could be utilized.

As shown in FIGS. 23 to 24b, the excision and aspiration assembly 6012 also includes a stationary inner sleeve 6254 having an axial opening 6256 for receiving the distal end 6182 of suction tube 6180. The inner sleeve 6254 is received within channel opening 6126 of outer tube 6120. The inner sleeve 6254 also includes a pair of spaced-apart lumen openings 6258a, 6258b therethrough. The lumen opening 6258a is used to receive the upper and lower adjustment wires 6234a, 6236a and the lumen opening 6258b is used to receive the upper and lower adjustment wires 6234b, 6236b. The suction tube opening 6178 of suction tube 6180 is in a proximate and adjacent position to each of the adjustment tracks 6250a, 6250b of cutting assembly 6220 (see FIG. 23). Each of the proximal ends 6240a, 6240b of the upper adjustment wires 6234a, 6234b are joined together to form a single upper adjustment wire 6234s for connection with the finger trigger 6028. Also, each of the proximal ends 6246a, 6246b of the lower adjustment wires 6236a, 6236b are joined together to form a single lower adjustment wire 6236s for connection with the finger trigger 6028. These aforementioned upper and lower adjustment wire connections 6234s and 6236s attached to the finger trigger 6028 allows for maneuvering of the rotating loop member 6222 for a specific depth of excision of tissue, as well as for the pulling of the cutting edge 6230 of loop ember 6222 towards the suction tube opening 6178 of suction tube 6180 in order to sever and excise a small portion of tissue from a patient.

In operation, the bipolar RF excision and aspiration device 6010 operates in the following manner, as referenced in FIGS. 23 to 24b, which illustrates the steps involved in a method of excising and aspirating a small portion of affected tissue (not shown) for removal by device 6010. With references to FIGS. 24 and 24a, the practitioner actuates device 6010 which initially extends the cutting assembly 6220 to its extended position $W_1$. After the initial actuation of the cutting assembly 6220, the practitioner partially depresses the finger trigger 6028 for the rotating of the cutting edge 6230 of loop member 6222 to a specified orientation in order to select a specific amount of depth of tissue to be excised. The specified orientation that is needed for the adjustment of the cutting edge 6230 of loop member 6222 on the affected tissue is accomplished by the pushing or pulling of the upper and lower adjustment wires 6234a, 6236a, 6234b, 6236b by the slight manipulation of the finger trigger 6028 in order to adjust for the desired depth of tissue being excised. The suction tube opening 6178 of suction tube 6180 is then placed in contact with the affected tissue (not shown). The suction tube opening 6178 them forms a vacuum seal with the tissue to be excised and aspirated (see FIG. 24a), where a small portion of the tissue is then pulled into the suction tube opening 6178 in preparation of cutting the tissue by the RF energy. As shown in FIG. 24b, the practitioner now fully depresses the finger trigger 6028 whereby all four adjustment wires 6234a, 6236a, 6234b, 6236b are in their set arrangement in order to pull back the cutting edge 6230 of loop member 6222 towards the suction tube opening 6178 of suction tube 6180. During such movement of the loop member 6229, its cutting edge 6230 cuts, scoops-out and excises (via the RF energy) a specific amount of tissue. The RF energy between the positive (+) electrode (the U-shaped cutting edge 6230) and the return negative (−) electrode (the suction tube 6180) allows for the scooping-out and excising of the tissue matter to proceed smoothly and efficiently. After removing the device 6010 from the tissue surface, the practitioner now releases the finger trigger 6028, where then the suction tube opening 6178 of suction tube 6180 pulls the excised tissue into the suction tube 6180, from where it is delivered to the tissue collection reservoir (not shown). With the release of the finger trigger 6028 (see FIG. 23), each of the upper and lower adjustment wires 6234a, 6236a, 6234b, 6236b move outwardly, allowing the cutting assembly 6220 to be in its extended position $W_2$ once again.

An eighth exemplary embodiment of the present invention is illustrated in FIGS. 25 to 28. Elements illustrated in FIGS. 25 to 28 which correspond to the elements described above with reference to FIGS. 6 to 8c have been designated by corresponding reference numbers increased by six thousand. The eighth embodiment is constructed in the same manner embodiment 1010 unless it is otherwise stated.

With reference to FIGS. 25 to 28, a bipolar excision and aspiration device 7010 includes an excision and aspiration assembly 7012 having a cutting assembly 7270 which is movable from an extended position $V_1$ to a retracted position $V_2$. The cutting assembly 7270 includes a pair of adjustment wires 7272a, 7272b each having a distal end 7274a, 7274b and a proximal end 7276a, 7276b. Each of the distal ends 7274a, 7274b of adjustment wires 7272a, 7272b includes a connector receptacle 7278a, 7278b for attachment to a pair of opposing ends 7280a, 7280b of a cutting wire 7282. Each of the proximal ends 7276a, 7276b of adjustment wires 7272a, 7272b are joined together to form a single adjustment wire 7272s for connection with finger trigger 7028. The cutting assembly 7270 further includes a loop guide member 7284 for use in positioning the cutting wire 7282 on the tissue (not shown) to be selected. The loop guide member 7284 includes a front rectangularly-shaped bar member 7286 and a pair of angled adjustment track 7288a, 7288b each having a longitudinal channel opening 7290a, 7290b therein. Each of the angled adjustment track 7288a, 7288b are integrally connected on opposing sides 7254a, 7254b of the outer tube 7120 at its distal end 7122 (see FIGS. 25 and 26). The opposing ends 7280a, 7280b of cutting wire 7282 and received within each of the channel openings 7290a, 7290b of adjustment tracks 7288a, 7288b, respectively (see FIG. 25). The cutting wire 7282 is then able to slide inwardly along the channel openings 7290a, 7290b of adjustment tracks 7288a, 7288b as the finger trigger 7028 actuates the pulling of adjustment wires 7272a, 7272b in an inwardly manner. The cutting assembly 7270 also includes a grasper/forceps member 7292 for grasping a small portion of tissue to be excised. The grasper member 7292 includes a pair of grasper arms 7294a, 7294b thereto. Each of the grasper arms 7294a, 7294b includes a distal end 7296a, 7296b and a proximal end 7298a, 7298b. Each of the distal ends 7296a, 7296b of arms 7294a, 7294b includes a grasping claw 7300a, 7300b, respectively, thereon for clasping onto a small portion of tissue matter. The grasper member 7292 is also moveable from an extended position $V_3$ to a retracted position $V_4$ depending upon the depth and amount of tissue to be excised. The degree of retraction (pulling back) of the grasping claws 7300a, 7300b (towards the suction tube opening 7178 of suction tube 7180) is accomplished by the slight manipulations of the finger trigger 7028 which allows for the determination of the exact amount of tissue to be excised. The depth of tissue excision is determined and controlled by how much the grasping claws 7300a, 7300b are capable for pulling up the tissue (away from the tissue surface) prior to excision. The proximal ends 7298a, 7298b of the grasper arms 7294a, 7294b includes a coiled spring mechanism 7302 for the opening and closing of the grasping claws 7300a, 7300b prior to the excising of the tissue. The proximal ends 7298a, 7298b of the grasper arms 7294a, 7294b are also attached to an actuation cable 7304 for actuating the coiled spring mechanism 7302. The actuation cable 7304 includes a distal end 7306 being attached to the proximal ends 7298a, 7298b of the grasper arms 7294a, 7294b and a proximal end 7303 being attached to the finger trigger 7028 (see FIGS. 25 and 28), thereby enabling the grasper member 7292 to clasp a specific amount of tissue prior to excising it.

Figure 26:
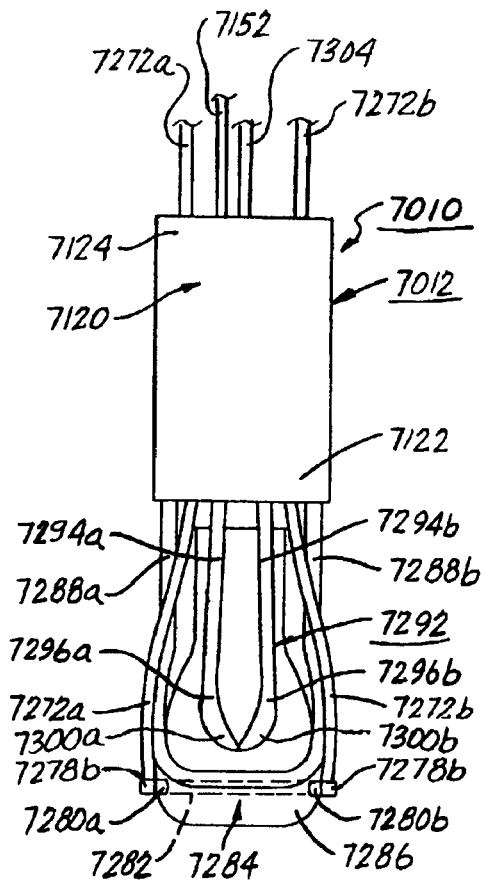
FIG. 26 is a front elevational view of the bipolar RF excision device of FIG. 28 showing a cutting wire loop and a tissue grasper in a fully extended position.
Figure 27:
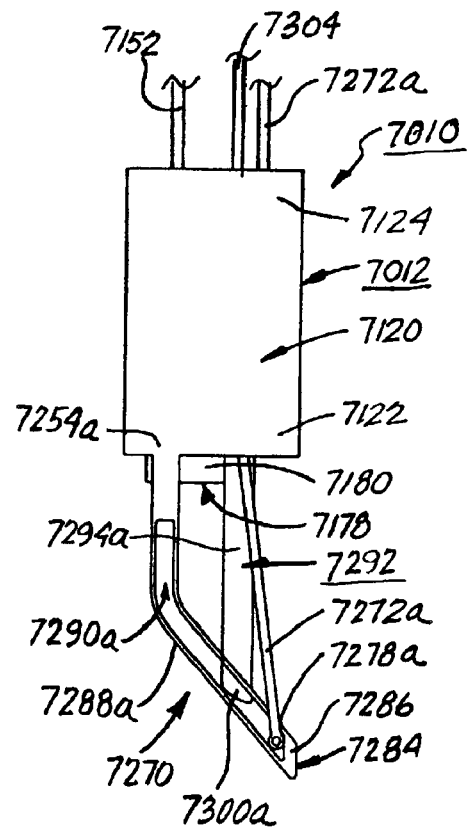
FIG. 27 is a side elevational view of the bipolar RF excision device of FIG. 28.

In operation, the bipolar RF excision and aspiration device 7010 operates in the following manner, as referenced in FIGS. 25 to 28, which illustrate the steps involved in a method of excising and aspirating a small portion of tissue matter (not shown) for removal by device 7010. With reference to FIGS. 25 to 28, the medical practitioner actuates device 7010 which initially extends the cutting wire 7282 being attached to the adjustment wires 7272a, 7272b to an extended position $V_1$ and simultaneously, extends the grasper arms 7294a, 7294b of grasper member 7292 to an extended position $V_3$ (see FIGS. 25 and 26). After the initial actuation, the practitioner partially depresses the finger trigger 7020 for grasping of the targeted tissue by the grasping claws 7300a, 7300b of the grasper member 7292 prior to excising it. As shown in FIGS. 25 and 26, the practitioner now retracts the oriented grasper member 7292 to the selected depth. Referring now to FIG. 28, the practitioner now fully depresses the finger trigger 7028, which then has the grasper member 7292 (in a first step) pulling and scooping a specific amount of tissue, and (in a successive second step) has the cutting wire 7292 advancing towards the suction tube opening 7178 of suction tube 7180. During such movement of the grasper member 7292 and the loop guide member 7284 uses the cutting wire 7292 for the scooping-out and excising (via the RF energy) of the pre-determined amount of tissue. The RF energy between the positive (+) electrode (the cutting wire 7282) and the return negative (−) electrode (the suction tube 7180) allows the scooping-out and excising of the tissue matter to proceed smoothly and efficiently.

The practitioner now removes the device 8010 from the tissue surface and then releases the finger trigger 7028. The suction tube opening 7178 of suction tube 7180 then pulls and aspirates the excised tissue matter into the suction tube 7180, from where it is delivered to the tissue collection reservoir (not shown). With the release of the finger trigger 7028 (see FIG. 25), each of the adjustment wires 7272a, 7272b move outwardly on adjustment tracks 7288a, 7288b, respectively, allowing the cutting wire 7282, as well as the grasper member 7292, to be in its extended positions $V_1$ and $V_3$ once again.

It should be understood that the embodiments described herein are merely exemplary and that a person skilled in the art may make many variations and modifications without departing from the spirit and scope of the present invention. All such variations and modifications are intended to be included within the scope of the invention as defined in the appended claims.

We claim:

1. An excision and aspiration apparatus adapted to sample a tissue mass, comprising:

receiving means for receiving a predetermined amount of tissue to be sampled, said receiving means being adapted to limit said predetermined amount to a superficial portion of the total tissue mass, said receiving means including a suction cup having a concave cavity sized and shaped to receive the superficial portion of the tissue mass;

excising means for excising the superficial portion of the tissue mass;

collection means for collecting the excised superficial portion of the tissue mass, wherein said collection means includes a suction tube, said suction cup being movably mounted in said suction tube between a first position, in which said suction cup extends across an opening in a tip of the suction tube and receives the superficial portion of the tissue mass under the influence of suction created by said suction means, and a second position away from said opening in which said suction cup releases the excised superficial portion of tissue mass under the influence of suction created by said suction means, said suction cup being pivotally mounted in the open-ended tip of said suction tube, whereby said suction cup is pivotable between its said first and second positions; and suction means for creating suction within said collection means, said suction being sufficient to draw the excised superficial portion of the tissue mass into the collection means.

2. An excision and aspiration apparatus according to claim 1, wherein said suction cup pivots between its said first and second positions in response to the activation and deactivation of a thumb-activated trigger mechanism.

3. An excision and aspiration apparatus according to claim 2, wherein said concave cavity is positioned on one side of said suction cup, said suction cup including a passageway extending from an opposite side thereof to said concave cavity.

4. An excision and aspiration apparatus according to claim 1, further comprising a RF energy source, said excising means functioning as a positive electrode for said RF energy source and said receiving means functioning as a negative electrode for said RF energy source.

5. An excision and aspiration apparatus according to claim 1, wherein said excising means includes a rotatable cutting blade.

6. An excision and aspiration apparatus according to claim 1, wherein said excising means includes a pair of cutting arms mounted for movement toward and away from each other.

7. An excision and aspiration apparatus according to claim 1, wherein said excising means includes a pair of rotatable cutting arms, each arm having a generally U-shaped cutting edge.

8. An excision and aspiration apparatus according to claim 1, wherein said excising means includes a looped-shaped cutting member which is pivotally mounted relative to said receiving means.

9. An excision and aspiration apparatus according to claim 1, wherein said receiving means includes a pair of tong-like graspers.

10. An excision and aspiration apparatus according to claim 1, wherein said suction cup has a passageway extending from said concave cavity to a surface opposite thereto, said passageway having a cross-sectional area significantly smaller than that of said suction tube.

11. An excision and aspiration apparatus adapted to sample a tissue mass, comprising:

receiving means for receiving a predetermined amount of tissue to be sampled, said receiving means being adapted to limit said predetermined amount to a superficial portion of the total tissue mass, said receiving means including a suction cup having a concave cavity sized and shaped to receive the superficial portion of the tissue mass, said concave cavity being positioned on one side of said suction cup, said suction cup including a passageway extending from an opposite side thereof to said concave cavity;

excising means for excising the superficial portion of the tissue mass;

collection means for collecting the excised superficial portion of the tissue mass, wherein said collection means includes a suction tube, said suction cup being movably mounted in said suction tube and moveable between a first position, in which said suction cup receives the superficial portion of the tissue mass under the influence of suction created by said suction means, and a second position, in which said suction cup releases the excised superficial portion of the tissue mass under the influence of suction created by said suction means, said suction cup being pivotally mounted in the open-ended tip of said suction tube, whereby said suction cup is pivotable between its said first and second positions in response to the activation and deactivation of a thumb-activated trigger mechanism; and said suction cup being oriented in a substantially transverse orientation relative to said suction tube when said suction cup is in its said first position, whereby said passageway is substantially exposed to the suction created by said suction means when said suction cup is in its first position; and wherein said suction cup is oriented in a substantially axial orientation relative to said suction tube when said suction cup is in its said second position, whereby said passageway is substantially shielded from the suction created by said suction means when said suction cup is in its said second position; and suction means for creating suction within said collection means, said suction being sufficient to draw the excised superficial portion of the tissue mass into the collection means.

12. An excision and aspiration apparatus according to claim 11, wherein said excising means includes a cutting wire which is mounted for reciprocating movement across an opening in said tip of said suction tube, said cutting wire being positioned between said opening and said suction cup.

13. An excision and aspiration apparatus according to claim 12, wherein said cutting wire is reciprocated in response to the activation and deactivation of a finger-activated trigger mechanism.

14. An excision and aspiration apparatus according to claim 13, wherein said collection means includes an external chamber connected to said suction tube.

15. An excision and aspiration apparatus according to claim 14, wherein said suction means includes a vacuum source connected to said external chamber of said collection means.

* * * * *